(12) United States Patent
Chen

(10) Patent No.: US 12,208,066 B2
(45) Date of Patent: Jan. 28, 2025

(54) METHODS OF PERMEABILIZING THE BLOOD BRAIN BARRIER

(71) Applicant: NeOnc Technologies, Inc., Los Angeles, CA (US)

(72) Inventor: Thomas Chen, La Canada, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 18/190,416

(22) Filed: Mar. 27, 2023

(65) Prior Publication Data

US 2023/0233481 A1   Jul. 27, 2023

Related U.S. Application Data

(63) Continuation of application No. 16/967,549, filed as application No. PCT/US2019/017076 on Feb. 7, 2019, now abandoned.

(60) Provisional application No. 62/716,190, filed on Aug. 8, 2018, provisional application No. 62/627,933, filed on Feb. 8, 2018.

(51) Int. Cl.

| | | |
|---|---|---|
| A61K 31/045 | (2006.01) | |
| A61K 9/00 | (2006.01) | |
| A61K 31/4015 | (2006.01) | |
| A61K 31/415 | (2006.01) | |
| A61K 31/4188 | (2006.01) | |
| A61K 31/4745 | (2006.01) | |
| A61K 35/17 | (2015.01) | |
| A61K 39/00 | (2006.01) | |
| A61K 39/395 | (2006.01) | |
| A61K 45/06 | (2006.01) | |
| A61P 35/00 | (2006.01) | |
| C07K 14/705 | (2006.01) | |
| C07K 16/28 | (2006.01) | |
| C07K 16/42 | (2006.01) | |
| C12N 5/0783 | (2010.01) | |
| C12N 5/16 | (2006.01) | |
| C12P 5/00 | (2006.01) | |

(52) U.S. Cl.
CPC .......... *A61K 31/045* (2013.01); *A61K 9/0019* (2013.01); *A61K 9/0043* (2013.01); *A61K 9/0078* (2013.01); *A61K 9/0085* (2013.01); *A61K 31/4015* (2013.01); *A61K 31/415* (2013.01); *A61K 31/4188* (2013.01); *A61K 31/4745* (2013.01); *A61K 39/3955* (2013.01); *A61K 39/4611* (2023.05); *A61K 39/4631* (2023.05); *A61K 39/464412* (2023.05); *A61K 45/06* (2013.01); *A61P 35/00* (2018.01); *C07K 14/70503* (2013.01); *C07K 16/2809* (2013.01); *C07K 16/42* (2013.01); *C12N 5/0638* (2013.01); *A61K 2039/505* (2013.01); *A61K 2039/54* (2013.01); *A61K 2039/543* (2013.01); *A61K 2039/544* (2013.01); *A61K 2039/545* (2013.01); *A61K 2239/31* (2023.05); *A61K 2239/38* (2023.05); *A61K 2239/48* (2023.05); *C07K 2317/52* (2013.01); *C12N 5/16* (2013.01); *C12P 5/007* (2013.01)

(58) Field of Classification Search
CPC .. A61K 31/045; A61K 9/0019; A61K 9/0043; A61K 9/0078; A61K 9/0085; A61K 31/4015; A61K 31/415; A61K 31/4188; A61K 31/4745; A61K 35/17; A61K 39/3955; A61K 45/06; A61K 2039/505; A61K 2039/54; A61K 2039/543; A61K 2039/544; A61K 2039/545; A61P 35/00; C07K 14/70503; C07K 16/2809; C07K 16/42; C07K 2317/52; C12N 5/0638; C12N 5/16
See application file for complete search history.

(56) References Cited

U.S. PATENT DOCUMENTS

| | | |
|---|---|---|
| 8,507,734 B2 | 8/2013 | Chen et al. |
| 2010/0226913 A1 | 9/2010 | Chen et al. |

FOREIGN PATENT DOCUMENTS

| | | |
|---|---|---|
| CN | 103946202 A | 7/2014 |
| JP | 2002097137 A | 4/2002 |
| JP | 2004526687 A | 9/2004 |
| JP | 2005533767 A | 11/2005 |
| JP | 2007302572 A | 11/2007 |
| JP | 2013522184 A | 6/2013 |
| JP | 2014505008 A | 2/2014 |
| JP | 2014507391 A | 3/2014 |
| JP | 2015502352 A | 1/2015 |
| WO | 2015/151123 A1 | 10/2015 |
| WO | 2017/152054 A1 | 9/2017 |

OTHER PUBLICATIONS

Brown, C. E., Aguilar, B., Starr, R., Yang, X., Chang, W. C., Weng, L., et al. Optimization of IL13Ra2-targeted chimeric antigen receptor t cells for improved anti-tumor efficacy against glioblastoma. Jan. 3, 2018; Mol. Ther. 26, 31-44 (Year: 2018).*
Carruthers et al., Abrogation of radioresistance in glioblastoma stem-like cells by inhibition of ATM kinase, Molecular Oncology, 9: 192-203, 2015 (Year: 2015).*
Cho HY, Wang W, Jhaveri N, et al. Perillyl alcohol for the treatment of temozolomide-resistant gliomas. Mol Cancer Ther. 2012;11(11):2462-2472 (Year: 2012).*
Dolgin E. Cancer Discovery, News in Brief, 926, Sep. 2017 (Year: 2017).*
Wang et al., Neuro-Oncology, 23(1):63-75, 2021 (Year: 2021).*
"Research progress on feed utilization of medicinal and edible plant perilla and its straw" Gansu Animal Husbandry and Veterinary, Issue 3, Issue 47, 2017, pp. 54-57.

(Continued)

*Primary Examiner* — Kimberly Ballard
*Assistant Examiner* — Stacey N Macfarlane
(74) *Attorney, Agent, or Firm* — Leason Ellis LLP

(57) ABSTRACT

The present invention relates to using monoterpene or sesquiterpene to permeabilize the blood brain barrier.

13 Claims, 13 Drawing Sheets

(56) References Cited

OTHER PUBLICATIONS

Chen et al.: "Perillyl Alcohol and Its Drug-Conjugated Derivatives as Potential Novel Methods of Treating Brain Metastases": Int J Mol Sci. Sep. 2, 2016;17(9):1463. doi: 10.3390/ijms17091463.

Terrell-Hall TB, Nounou MI, El-Amrawy F, Griffith JIG, Lockman PR. Trastuzumab distribution in an in-vivo and in-vitro model of brain metastases of breast cancer. Oncotarget. Jul. 26, 2017;8(48):83734-837 44. doi: 10.18632/oncotarget.19634. (Year: 2017).

Hanson and Frey, "Intranasal delivery bypasses the blood-brain barrier to target therapeutic agents to the central nervous system and treat neurodegenerative disease", 2008, BMC Neuroscience, vol. 9, pp. 1-4.

Chuntova et al.: "Genetically Engineered T-Cells for Malignant Glioma: Overcoming the Barriers to Effective Immunotherapy": Frontiers in Immunology; Jan. 22, 2019; vol. 9; Article 3062; pp. 1-19. [19 pages].

\* cited by examiner

The comparison of CD3 positive cells in the brain tumor after 2-million human CAR T cells delivered by intravenous injection. A. Intravenous injection CAR T cells only; B: Combination of intracardiac of 3% NEO100 with intravenous injection of CAR T cells.

CD3 expression on cultured human CAR T cells – Cytoprep

CD3 staining in normal C57 BL/6 brain section

CD3 expression in brain with GL261 mouse glioma
(2x10$^6$ Lym-1 human CAR T cells were given by intravenous injection)

CD3 expression in brain with GL261 mouse glioma (2x10$^6$ Lym-1 human CAR T cells injected by IV after IC injection of 3% NEO100)

CD3 expression in brain with GL261 mouse glioma (2x10$^6$ Anti-CD19 human CAR T cells were given by intravenous injection)

CD3 expression in brain with GL261 mouse glioma (2x10$^6$ Anti-CD19 human CAR T cells injected by IV after IC injection of 3% NEO100)

The comparison of CD3 positive cells in the normal part of brain with GL261 tumor IC 5%NEO100    Normal

METHODS OF PERMEABILIZING THE BLOOD BRAIN BARRIER

CROSS REFERENCE TO RELATED APPLICATIONS

This application is a Continuation of U.S. application Ser. No. 16/967,549, filed Aug. 5, 2020, which is a National Stage of PCT/US2019/017076, filed Feb. 7, 2019, which claims benefit of U.S. Provisional Patent Application Nos. 62/627,933, filed Feb. 8, 2018 and 62/716,190, filed Aug. 8, 2018. The disclosures of these applications are herein incorporated by reference in their entirety.

FIELD OF THE INVENTION

The present invention relates to using monoterpene or sesquiterpene to permeabilize the blood brain barrier.

BACKGROUND OF THE INVENTION

The blood brain barrier (BBB) is a continuous boundary between the blood, the interstitial fluid (IF) and the cerebrospinal fluid (CSF) of the brain. It is composed of a layer of endothelial cells, the cerebral capillary endothelium, that serves as an effective barrier against the entry into the brain's tissue of serum components of both high and low molecular sizes. The restriction against entry of such substances into the brain and the CSF is due to the unique structure of the cerebral capillary endothelium. While in other organs the cells of the endothelial layer have gaps and channels between them that run all the way through the layer, such channels are lacking in the cerebral capillary endothelium which is unique both in terms of the anatomically tight junctions between its cells and in terms of the rarity of pinocytic vesicles that can be frequently seen in other endothelia.

In a normal (healthy) state, only substances capable of traversing the BBB can enter the brain and such substances tend to be relatively hydrophobic (lipid-like). Substances which are hydrophilic (water-soluble) penetrate the BBB much less effectively or not at all. Such water-soluble and poorly penetrating substances encompass a whole range of molecules extending from molecules as large as albumin to ions as small as sodium, as well as chemotherapeutic agents, drugs, diagnostic imaging compounds and proteins of potential therapeutic use. While some therapeutic agents have sufficient degrees of lipid-solubility to penetrate the BBB, the great majority of drugs (e.g., penicillin) and other therapeutically useful substances have limited lipid solubility, hence cannot penetrate the BBB well. This poor permeability of BBB by many potentially useful drugs poses a severe limitation on the treatment of diseases of the brain tissue and CSF. It is therefore of paramount clinical significance to develop products and methods which would "open" the BBB and allow access to the brain tissues and CSF by agents which are known to be effective in treating or diagnosing brain disorders but which, on their own, would not be able to traverse the BBB.

Malignant gliomas, the most common form of central nervous system (CNS) cancers, are currently considered essentially incurable. Among the various malignant gliomas, anaplastic astrocytomas (Grade III) and glioblastoma multiforme (GBM; Grade IV) have an especially poor prognosis due to their aggressive growth and resistance to currently available therapies. The present standard of care for malignant gliomas consists of surgery, ionizing radiation, and chemotherapy. Despite recent advances in medicine, the past 50 years have not seen any significant improvement in prognosis for malignant gliomas. Wen et al. Malignant gliomas in adults. *New England J Med.* 359:492-507, 2008. Stupp et al. Radiotherapy plus concomitant and adjuvant temozolomide for glioblastoma. *New England J Med.* 352: 987-996, 2005.

A major reason for the poor prognosis of malignant gliomas is the difficulty in delivering a sufficient quantity of chemotherapeutic agents to the brain. Drug access to the brain is limited by the blood brain barrier (BBB). The concentration of drugs that finally reach the brain is further decreased by hepatic first-pass metabolism and urinary excretion. Therefore, invasive surgeries are often required, such as tumor resection, stereotactic injection of anti-tumor medication, or placement of catheters for convection enhanced delivery of medication.

Intranasal delivery of a drug offers a novel non-invasive therapy to bypass the blood brain barrier and to rapidly deliver pharmaceutical agents to the CNS directly. Intranasally administered drugs reach the parenchymal tissues of the brain, spinal cord and/or cerebrospinal fluid (CSF) within minutes. In addition to delivery via the olfactory tract and trigeminal nerves, it appears from animal studies that the therapeutic drug is also delivered systemically through the nasal vasculature. Hashizume et al. New therapeutic approach for brain tumors: intranasal delivery of telomerase inhibitor GRN163. *Neuro-oncology* 10:112-120, 2008. Thorne et al. Delivery of insulin-like growth factor-1 to the rat brain and spinal cord along olfactory and trigeminal pathways following intranasal administration. *Neuroscience* 127:481-496, 2004. Intranasal delivery of therapeutic agents may provide a systemic method for treating other types of cancers, such as lung cancer, prostate cancer, breast cancer, hematopoietic cancer and ovarian cancer, etc.

Despite decades of attempts, curative immunological therapy against cancer has been very difficult to achieve, with the fundamental basis being antigen-recognition capacity, either by antibodies or through T cells (via the T cell receptor) (Cousin-Frankel, Science (2013) 342:1432). Antibody-based immunotherapies have been used extensively against cancer in instances where the target antigen is up-regulated in tumor cells as compared to normal cells (e.g., Her-2 in Her-2 amplified breast cancer), or in cases where the tumor cells express an antigen that can be recognized by the antibody or an antibody-toxin conjugate (e.g., Rituximab against CD20) (Baselga et al., *Annals Oncology* (2001) 12: S35). While clinical trials using antibody-based immunotherapies have shown improved patient survival in a limited number of cancer types (usually when combined with standard chemotherapy), these effects are often accompanied by significant safety and efficacy concerns (Cousin-Frankel Cancer, *Science* (2013) 342:1432).

Effective T cell therapies against cancers have been even more difficult to achieve clinically (Schmitt et al., *Hum. Gene Ther.* (2009) 20 (11): 1240). An effective T cell therapy against cancer relies on a T cell with a high affinity binding directed against an antigen on a cancer cell. Chimeric antigen receptor T cells (CAR T cells) are widely used to recognize antigens on cells with both high affinity and specificity and without the requirement for accessory recognition molecules, such as HLA antigens to "present" peptides. The T cell receptor of a CAR T cells is "swapped" with an antigen-binding heavy and light chains, thereby obviating the need for HLA accessory molecules. The recombinant CAR T receptor is fused to signaling domains leading to activation of the T cell upon binding of the CAR T receptor to the target antigen.

Perillyl alcohol (POH), a naturally occurring monoterpene, has been suggested to be an effective agent against a variety of cancers, including CNS cancer, breast cancer, pancreatic cancer, lung cancer, melanomas and colon cancer. Gould, M. Cancer chemoprevention and therapy by monoterpenes. Environ Health Perspect. 1997, 105 (Suppl 4): 977-979. Hybrid molecules containing both perillyl alcohol and retinoids were prepared to increase apoptosis-inducing activity. Das et al. Design and synthesis of potential new apoptosis agents: hybrid compounds containing perillyl alcohol and new constrained retinoids. Tetrahedron Letters 2010, 51, 1462-1466.

There is still a need to permeabilize the blood brain barrier for delivery of various therapeutic agents, in the treatment of cancers such as malignant gliomas, as well as other brain disorders such as Parkinson's and Alzheimer's disease.

SUMMARY OF THE INVENTION

The present invention provides for a method of administering a therapeutic agent to a central nervous system of a mammal (e.g., a human), the method comprising administering a monoterpene before, after or concurrently with the therapeutic agent.

The central nervous system may be the brain.

The monoterpene may be perillyl alcohol.

The monoterpene (e.g., perillyl alcohol) may be administered into a vascular system of the mammal such as intraarterially (e.g., injected into an artery). The monoterpene (e.g., perillyl alcohol) may be administered by inhalation, intranasally, orally, intravenously, subcutaneously or intramuscularly.

The monoterpene (e.g., perillyl alcohol) may be administered at a dose ranging from about 0.050 mg/kg to about 500 mg/kg of body weight.

The monoterpene (e.g., perillyl alcohol) may be administered from about 0.2 minutes to about 60 minutes or administered from about 1 minute to about 15 minutes, before the therapeutic agent is administered.

The monoterpene and the therapeutic agent may be administered separately.

The monoterpene and the therapeutic agent may be administered concurrently. In one embodiment, the monoterpene and the therapeutic agent are administered together in a pharmaceutical composition (e.g., a solution).

The therapeutic agent may be a chemotherapeutic agent. Non-limiting examples of chemotherapeutic agents include a DNA alkylating agent, a topoisomerase inhibitor, an endoplasmic reticulum stress inducing agent, a platinum compound, an antimetabolite, an enzyme inhibitor, a receptor antagonist, a therapeutic antibody, and combinations thereof. The chemotherapeutic agent may be dimethylcelecoxib (DMC), irinotecan (CPT-11), temozolomide or rolipram.

The therapeutic agent may be an antibody or antibody fragment.

The therapeutic agent may be an immune cell expressing a chimeric antigen receptor. The immune cell may be a T cell. In one embodiment, the therapeutic agent is a CAR-T cell.

The mammal may have cancer, such as a tumor of the nervous system (e.g., a glioblastoma).

The method may further comprise the step of treating the mammal with radiation.

BRIEF DESCRIPTION OF THE DRAWINGS

FIG. 2A shows immunohistochemistry (IHC) staining to detect the penetration of human CAR T cells inside the brain and the tumor formed (GL261 mouse glioma). The primary antibody, Anti-Human CD3 antibody (CD3ε(D7A6E™) XP® Rabbit mAb (#85061) (Cell Signaling, Boston, MA), was used to identify human derived CD3 positive cells.

FIG. 4A shows an in vitro brain barrier tight junction model. The labelled components are Transwell chemotaxis chamber; upper chamber; porous membrane and lower chamber. Transwell culture chambers (pore size: 0.8 μm). Madin-Darby Canine Kidney (MDCK) cells are epithelial cells. TEER: transepithelial/transendothelial electrical resistance. Fluorescence Ab: Alexa Fluo®488; donkey anti-rat IgG (H+L). Fluorescence was measured in the lower chamber in about 120 minutes. FIG. 4B shows the enhanced penetration of fluorescence labelled antibody through the upper chamber with increased concentrations. FIG. 4C shows the decreased TEER after application of NEO100 at a concentration of 2 mM. FIG. 4D shows the recovery time of TEER post the application of NEO100.

Figure 1:
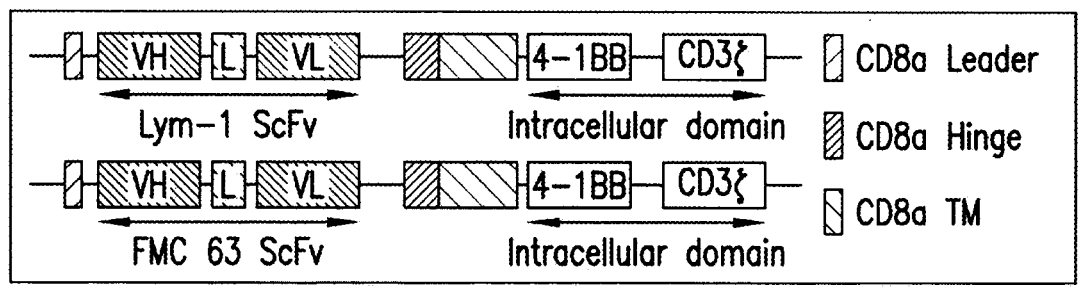
FIG. 1 shows the schematic representation of Lym-1 CAR and CD19 (FMC 63) CAR constructs.
Figure 2A:
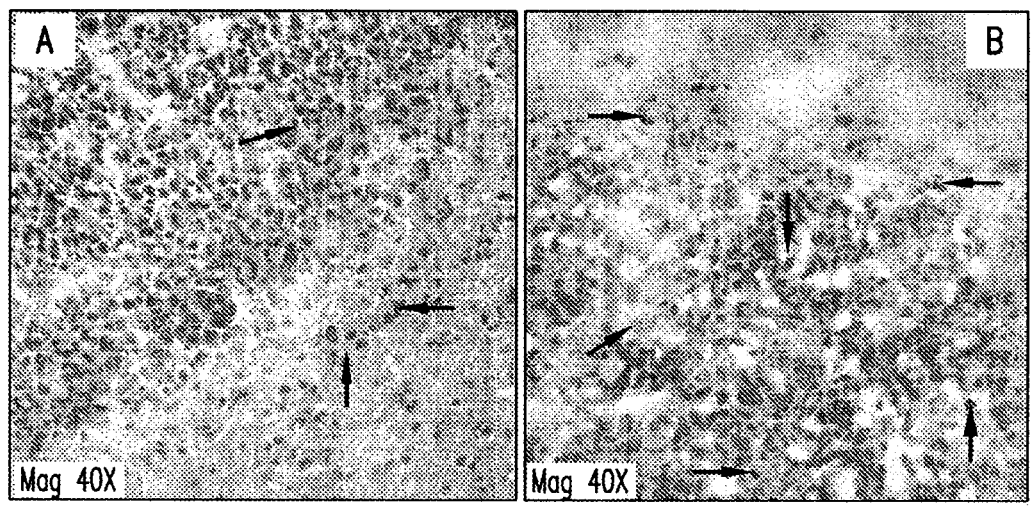
FIG. 2A shows accumulation of human CAR T cells inside the brain tumor.
Figure 2B:
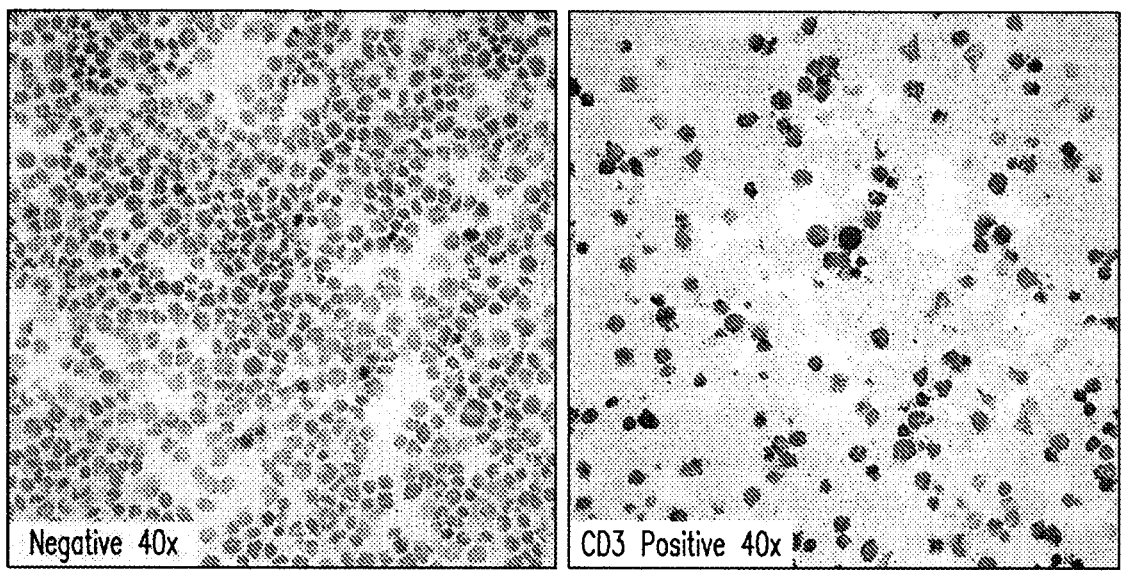
FIG. 2B shows CD3 expression on cultured human CAR T cells.
Figure 2C:
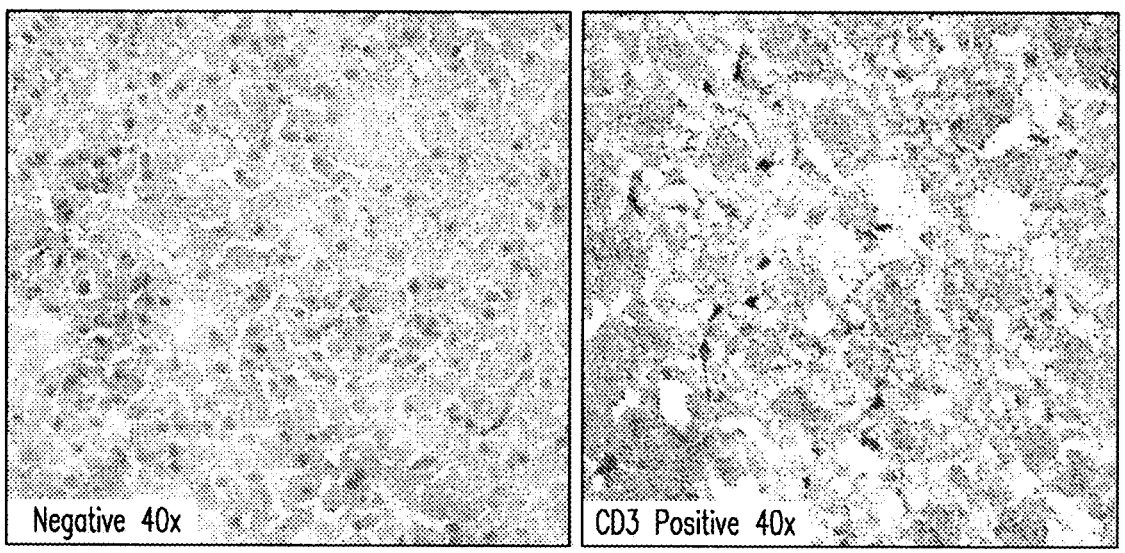
FIG. 2C shows CD3 staining in normal C57 BL/6 brain section.
Figure 2D:
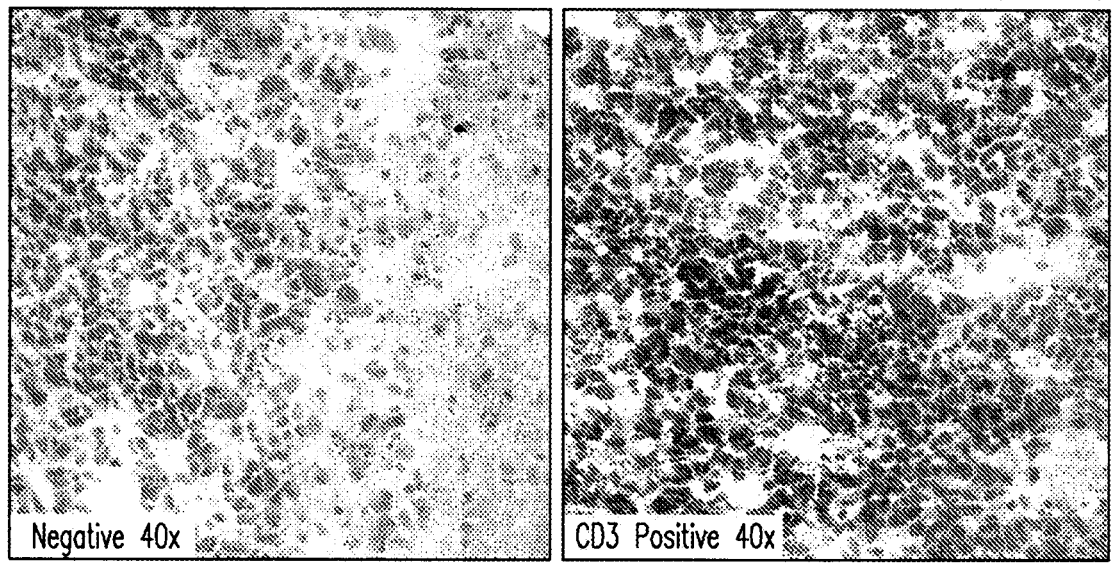
FIG. 2D shows CD3 expression in the brain with GL261 mouse glioma, when Lym-1 human CAR T cells were given by intravenous (IV) injection.
Figure 2E:
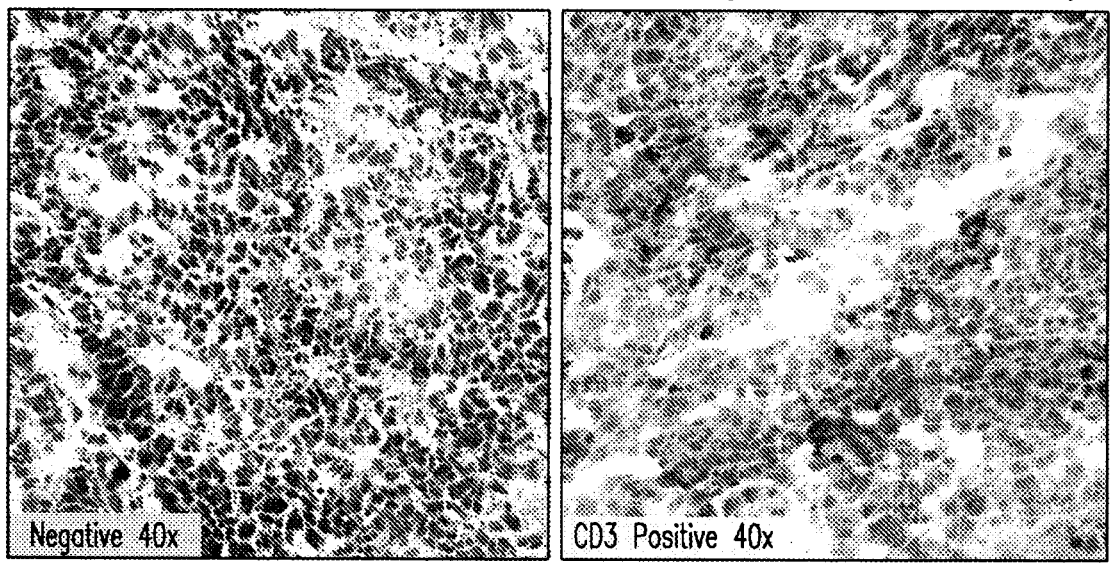
FIG. 2E shows CD3 expression in the brain with GL261 mouse glioma, when Lym-1 human CAR T cells were injected by IV after IC injection of 3% NEO100.
Figure 2F:
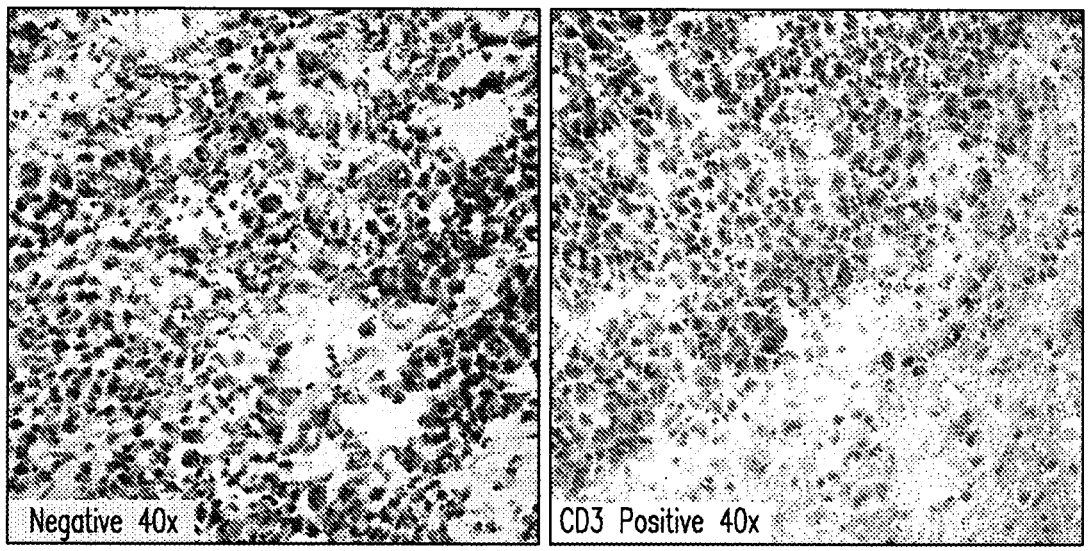
FIG. 2F shows CD3 expression in the brain with GL261 mouse glioma, when anti-CD19 human CAR T cells were given by intravenous (IV) injection.
Figure 2G:
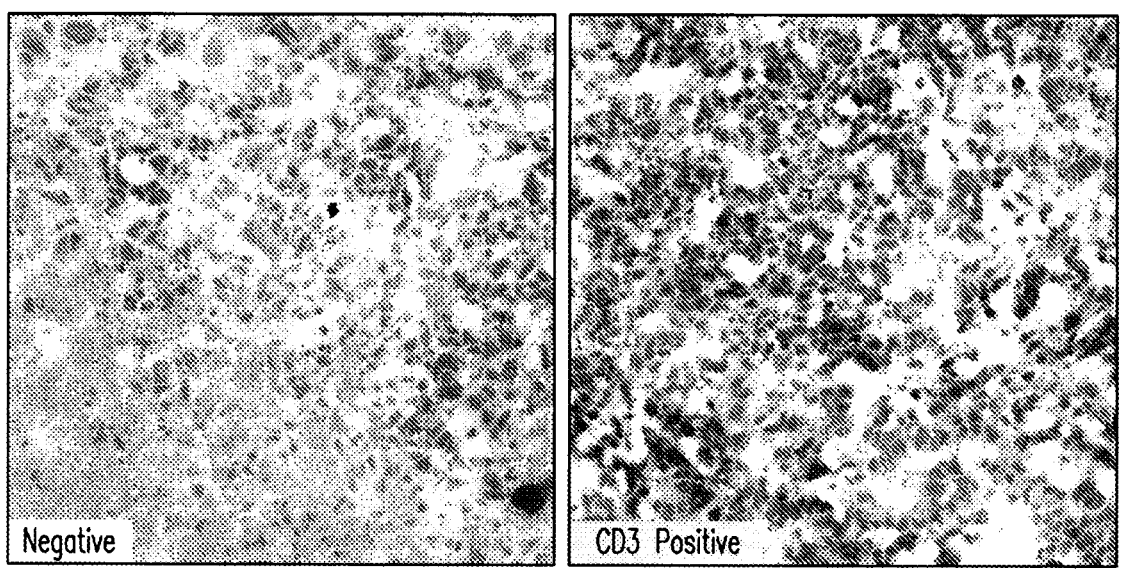
FIG. 2G shows CD3 expression in the brain with GL261 mouse glioma, when anti-CD19 human CAR T cells were injected by IV after IC injection of 3% NEO100.
Figure 2H:
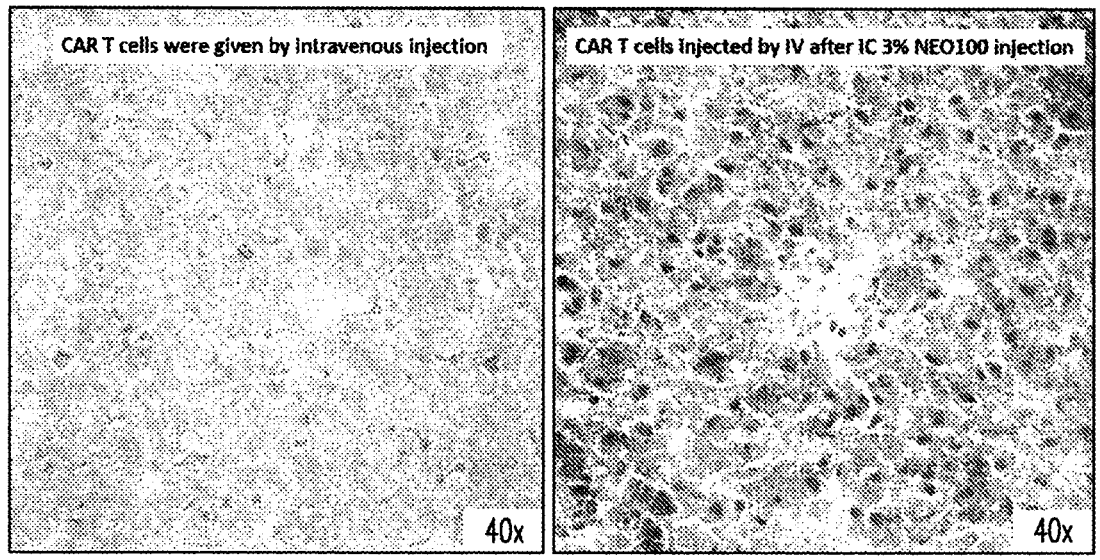
FIG. 2H shows the comparison of CD3 positive cells in the normal part of the brain with GL261 tumor.

As used herein, the term "NEO100" refer to perillyl alcohol.

DETAILED DESCRIPTION OF THE INVENTION

The present invention provides for methods of using monoterpene or sesquiterpene or their derivatives (e.g., perillyl alcohol or POH, isoperillyl alcohol, or perillyl alcohol derivatives) to permeabilize the blood brain barrier. Thus, monoterpene or sesquiterpene can be used to deliver at least one therapeutic agent across the BBB.

The monoterpene (or sesquiterpene) may have a purity of greater than about 98.5% (w/w), greater than about 99.0% (w/w), or greater than about 99.5% (w/w).

The monoterpene (or sesquiterpene) may be formulated into a pharmaceutical composition in the presence or absence of the therapeutic agent(s), where the monoterpene (or sesquiterpene) is present in amounts ranging from about 0.01% (w/w) to about 100% (w/w), from about 0.1% (w/w) to about 80% (w/w), from about 1% (w/w) to about 70% (w/w), from about 10% (w/w) to about 60% (w/w), from about 1% (w/w) to about 10% (w/w), from about 1% (w/w) to about 5% (w/w), from about 1% (w/w) to about 3% (w/w), from about 3% (w/w) to about 10% (w/w), or from about 0.1% (w/w) to about 20% (w/w).

The monoterpene (e.g., perillyl alcohol) may be administered at a dose ranging from about 0.050 mg/kg to about 500 mg/kg of body weight. Other ranges, include, about 0.1 mg/kg to about 100 mg/kg, about 1 mg/kg to about 50 mg/kg, about 5 mg/kg to about 25 mg/kg, and about 10 mg/kg to about 15 mg/kg.

The monoterpene or sesquiterpene may be used in combination with at least one therapeutic agents, including, but not limited to, chemotherapeutic agents, immunotherapeutic agents, immunomodulatory agents, antibodies (e.g., monoclonal antibodies), immune cells (e.g., CAR-T cells), vaccines, antibody-drug conjugates, antiviral agents, anti-inflammatory agents, antibacterial agents, antimicrobial agents, antibiotics, and combinations thereof.

The anti-cancer agents that may be used in combination with the purified monoterpene or sesquiterpene can have one or more of the following effects on cancer cells or the subject: cell death; decreased cell proliferation; decreased numbers of cells; inhibition of cell growth; apoptosis; necrosis; mitotic catastrophe; cell cycle arrest; decreased cell size; decreased cell division; decreased cell survival; decreased cell metabolism; markers of cell damage or cytotoxicity; indirect indicators of cell damage or cytotoxicity such as tumor shrinkage; improved survival of a subject; or disappearance of markers associated with undesirable, unwanted, or aberrant cell proliferation. U.S. Patent Publication No. 20080275057.

The therapeutic agent may be dissolved in perillyl alcohol. The present compositions can be administered alone, or may be co-administered together with radiation or another agent (e.g., a chemotherapeutic agent), to treat a disease such as cancer.

In some embodiments, the agent is an antibody-drug conjugate. In some embodiments, the antibody-drug conjugate comprises an antigen-binding fragment and a toxin or drug that induces cytotoxicity in a target cell. Toxins or drugs compatible for use in antibody-drug conjugate are well known in the art and will be evident to one of ordinary skill in the art. Sec, e.g., Peters et al. Biosci. Rep. (2015) 35 (4): e00225. In some embodiments, the antibody-drug conjugate may further comprise a linker (e.g., a peptide linker, such as a cleavable linker) attaching the antibody and drug molecule.

Treatments may be sequential, with the monoterpene (or sesquiterpene) being administered before or after the administration of the therapeutic agent(s). Alternatively, the monoterpene (or sesquiterpene) and the therapeutic agent(s) may be administered concurrently.

The monoterpene (or sesquiterpene) and at least one therapeutic agent may be administered simultaneously, separately, or sequentially. They may exert an advantageously combined effect (e.g., additive, or synergistic effects).

For sequential administration, either a monoterpene (or sesquiterpene) is administered first and then a therapeutic agent(s), or the therapeutic agent(s) is administered first followed by the monoterpene (or sesquiterpene). In embodiments where a monoterpene (or sesquiterpene) and a therapeutic agent are administered separately, administration of the monoterpene (or sesquiterpene) can precede administration, or, alternatively follow administration of the therapeutic agent(s) by seconds, minutes, hours, days, or weeks. The time difference in non-simultaneous administrations may be greater than 1 minute, and can be, for example, precisely, at least, up to, or less than, 5 minutes, 10 minutes, 15 minutes, 30 minutes, 45 minutes, 60 minutes, 2 hours, 3 hours, 6 hours, 9 hours, 12 hours, 24 hours, 36 hours, or 48 hours, or more than 48 hours. The two or more agents can be administered within minutes of each other or within about 0.5, about 1, about 2, about 3, about 4, about 6, about 9, about 12, about 15, about 18, about 24, or about 36 hours of each other or within about 1, 2, 3, 4, 5, 6, 7, 8, 9, 10, 12, 14 days of each other or within about 2, 3, 4, 5, 6, 7, 8, 9, or 10 weeks of each other. In some cases, longer intervals are possible.

The present disclosure also provides for a pharmaceutical composition comprising (i) at least one a monoterpene (or sesquiterpene); and (ii) at least one therapeutic agent.

The route of administration may vary, and can include, intraarterial delivery, inhalation, intranasal, oral, transdermal, intravenous, subcutaneous or intramuscular injection.

The present invention also provides for a method of treating a disease such as cancer, comprising the step of delivering to a patient the present composition.

The compositions of the present invention may contain one or more types of monoterpene (or sesquiterpene). Monoterpenes include terpenes that consist of two isoprene units and have the molecular formula $C_{10}H_{16}$. Monoterpenes may be linear (acyclic) or contain rings. Monoterpenoids, produced by biochemical modifications such as oxidation or rearrangement of monoterpenes, and pharmaceutically acceptable salts of monoterpenes or monoterpenoids, are also encompassed by the present invention. Examples of monoterpenes and monoterpenoids include, perillyl alcohol (S (−)) and R (+)), geranyl pyrophosphate, ocimene, myrcene, geraniol, citral, citronellol, citronellal, linalool, pinene, terpincol, terpinen, limonene, terpinenes, phellandrenes, terpinolene, terpinen-4-ol (or tea tree oil), pinene, terpineol, terpinen; the terpenoids such as p-cymene which is derived from monocyclic terpenes such as menthol, thymol and carvocrol; bicyclic monoterpenoids such as camphor, borneol and eucalyptol.

Monoterpenes may be distinguished by the structure of a carbon skeleton and may be grouped into acyclic monoterpenes (e.g., myrcene, (Z)- and (E)-ocimene, linalool, geraniol, nerol, citronellol, myrcenol, geranial, citral a, neral, citral b, citronellal, etc.), monocyclic monoterpenes (e.g., limonene, terpinene, phellandrene, terpinolene, menthol, carveol, etc.), bicyclic monoterpenes (e.g., pinene, myrtenol, myrtenal, verbanol, verbanon, pinocarveol, carene, sabinene, camphene, thujene, etc.) and tricyclic monoterpenes (e.g. tricyclene). See *Encyclopedia of Chemical Technology*, Fourth Edition, Volume 23, page 834-835.

Sesquiterpenes of the present invention include terpenes that consist of three isoprene units and have the molecular formula C15H24. Sesquiterpenes may be linear (acyclic) or contain rings. Sesquiterpenoids, produced by biochemical modifications such as oxidation or rearrangement of sesquiterpenes, are also encompassed by the present invention. Examples of sesquiterpenes include farnesol, farnesal, farnesylic acid and nerolidol.

The derivatives of monoterpene (or sesquiterpene) include, but are not limited to, esters, alcohols, aldehydes, and ketones of the monoterpene (or sesquiterpene). Monoterpene (or sesquiterpene) alcohols may be derivatized to esters, aldehydes, or acids.

Esters of the monoterpene (or sesquiterpene) alcohols of the present invention can be derived from an inorganic acid or an organic acid. Inorganic acids include, but are not limited to, phosphoric acid, sulfuric acid, and nitric acid. Organic acids include, but are not limited to, carboxylic acid such as benzoic acid, fatty acid, acetic acid and propionic acid. Examples of esters of monoterpene (or sesquiterpene) alcohols include, but are not limited to, carboxylic acid esters (such as benzoate esters, fatty acid esters (e.g., palmitate ester and linoleate ester), acetates, propionates (or propanoates), and formates), phosphates, sulfates, and carbamates (e.g., N,N-dimethylaminocarbonyl). Wikipedia-Ester. Retrieved from URL: en.wikipedia.org/wiki/Ester.

A specific example of a monoterpene that may be used in the present invention is perillyl alcohol (commonly abbreviated as POH). Perillyl alcohol compositions of the present invention can contain(S)-perillyl alcohol, (R)-perillyl alcohol, or a mixture of(S)-perillyl alcohol and (R)-perillyl alcohol.

The terms "chimeric receptor," "Chimeric Antigen Receptor," or alternatively a "CAR" are used interchangeably throughout and refer to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined below. Lec et al., *Clin. Cancer Res*. (2012) 18 (10): 2780; Jensen et al., *Immunol Rev*. (2014) 257 (1): 127; world wide web, cancer dot gov/about-cancer/treatment/research/car-t-cells. In one embodiment, the stimulatory molecule is the zeta chain associated with the T cell receptor complex. In one aspect, the cytoplasmic signaling domain further comprises one or more functional signaling domains derived from at least one costimulatory molecule as defined below. The costimulatory molecule may also be 4-1BB (i.e., CD137), CD27 and/or CD28 or fragments of those molecules. In another aspect, the CAR comprises a chimeric fusion protein comprising an extracellular antigen recognition domain, a transmembrane domain and an intracellular signaling domain comprising a functional signaling domain derived from a stimulatory molecule. The CAR comprises a chimeric fusion protein comprising an extracellular antigen recognition domain, a transmembrane domain and an intracellular signaling domain comprising a functional signaling domain derived from a co-stimulatory molecule and a functional signaling domain derived from a stimulatory molecule. Alternatively, the CAR comprises a chimeric fusion protein comprising an extracellular antigen recognition domain, a transmembrane domain and an intracellular signaling domain comprising two functional signaling domains derived from one or more co-stimulatory molecule(s) and a functional signaling domain derived from a stimulatory molecule. The CAR can also comprise a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule. The antigen recognition moiety of the CAR can contain any antigen-binding antibody fragment. The antibody fragment can comprise one or more CDRs, the variable region (or portions thereof), the constant region (or portions thereof), or combinations of any of the foregoing.

As used herein, a chimeric receptor refers to a non-naturally occurring molecule that can be expressed on the surface of a host cell and comprises an antigen-binding fragment. In general, chimeric receptors comprise at least two domains that are derived from different molecules. In addition to the antigen-binding fragment described herein, the chimeric receptor may further comprise one or more of a hinge domain, a transmembrane domain, at least one co-stimulatory domain, and a cytoplasmic signaling domain. In some embodiments, the chimeric receptor comprises from N terminus to C terminus, an antigen-binding fragment, a hinge domain, a transmembrane domain, and a cytoplasmic signaling domain. In some embodiments, the chimeric receptor further comprises at least one co-stimulatory domain.

In some embodiments, the chimeric receptors described herein comprise a hinge domain, which may be located between the antigen-binding fragment and a transmembrane domain. A hinge domain is an amino acid segment that is generally found between two domains of a protein and may allow for flexibility of the protein and movement of one or both of the domains relative to one another. Any amino acid sequence that provides such flexibility and movement of the antigen-binding fragment relative to another domain of the chimeric receptor can be used.

Any of the chimeric receptors described herein can be introduced into a suitable immune cell for expression via conventional technology. In some embodiments, the immune cells are T cells, such as primary T cells or T cell lines. Alternatively, the immune cells can be NK cells, such as established NK cell lines (e.g., NK-92 cells). In some embodiments, the immune cells are T cells that express CD8 (CD8+) or CD8 and CD4 (CD8$^+$/CD4$^+$). In some embodiments, the T cells are T cells of an established T cell line, for example, 293T cells or Jurkat cells.

In some embodiments, the immune cells expressing any of the chimeric receptors described herein are administered to a subject in an amount effective in to reduce the number of target cells (e.g., cancer cells) by least 20%, e.g., 50%, 80%, 100%, 2-fold, 5-fold, 10-fold, 20-fold, 50-fold, 100-fold or more.

A typical amount of cells, e.g., immune cells (such as CAR T cells), administered to a mammal (e.g., a human) can be, for example, in the range of one million to 100 billion cells; however, amounts below or above this exemplary range are also within the scope of the present disclosure. For example, the daily dose of cells can be about 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), preferably about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), more preferably about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells, or a range defined by any two of the foregoing values).

In one embodiment, the chimeric receptor (e.g., a nucleic acid encoding the chimeric receptor) is introduced into an immune cell, and the subject (e.g., human patient) receives an initial administration or dose of the immune cells expressing the chimeric receptor. One or more subsequent administrations of the agent (e.g., immune cells expressing the chimeric receptor) may be provided to the patient at intervals of 15 days, 14, 13, 12, 11, 10, 9, 8, 7, 6, 5, 4, 3, or 2 days after the previous administration. More than one dose of the agent can be administered to the subject per week, e.g., 2, 3, 4, or more administrations of the agent. The subject may receive more than one doses of the agent (e.g., an immune cell expressing a chimeric receptor) per week, followed by a week of no administration of the agent, and finally followed by one or more additional doses of the agent (e.g., more than one administration of immune cells expressing a chimeric receptor per week). The immune cells expressing a chimeric receptor may be administered every other day for 3 administrations per week for two, three, four, five, six, seven, eight or more weeks.

In the context of the present disclosure insofar as it relates to any of the disease conditions recited herein, the terms "treat," "treatment," and the like mean to relieve or alleviate at least one symptom associated with such condition, or to slow or reverse the progression of such condition. Within the meaning of the present disclosure, the term "treat" also denotes to arrest, delay the onset (i.e., the period prior to clinical manifestation of a disease) and/or reduce the risk of developing or worsening a disease. For example, in connection with cancer the term "treat" may mean eliminate or reduce a patient's tumor burden, or prevent, delay or inhibit metastasis, etc.

The methods and compositions described herein may be used to treat, without limitation, brain tumors, lung cancer, car, nose and throat cancer, hematopoietic cancers, colon cancer, melanoma, pancreatic cancer, mammary cancer, prostate cancer, breast cancer, ovarian cancer, basal cell carcinoma, biliary tract cancer; bladder cancer; bone cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; liver cancer; fibroma, neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas.

Carcinomas are cancers of epithelial origin. Carcinomas intended for treatment with the methods of the present disclosure include, but are not limited to, acinar carcinoma, acinous carcinoma, alveolar adenocarcinoma (also called adenocystic carcinoma, adenomyoepithelioina, cribriform carcinoma and cylindroma), carcinoma adenomatosum, adenocarcinoma, carcinoma of adrenal cortex, alveolar carcinoma, alveolar cell carcinoma (also called bronchiolar carcinoma, alveolar cell tumor and pulmonary adenomatosis), basal cell carcinoma, carcinoma basocellulare (also called basaloma, or basiloma, and hair matrix carcinoma), basaloid carcinoma, basosquamous cell carcinoma, breast carcinoma, bronchioalveolar carcinoma, bronchiolar carcinoma, bronchogenic carcinoma, cerebriform carcinoma, cholangiocellular carcinoma (also called cholangioma and cholangiocarcinoma), chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epibulbar carcinoma, epidermoid carcinoma, carcinoma epitheliale adenoides, carcinoma exulcere, carcinoma fibrosum, gelatiniform carcinoma, gelatinous carcinoma, giant cell carcinoma, gigantocellulare, glandular carcinoma, granulosa cell carcinoma, hair-matrix carcinoma, hematoid carcinoma, hepatocellular carcinoma (also called hepatoma, malignant hepatoma and hepatocarcinoma), Huirthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, lenticular carcinoma, carcinoma lenticulare, lipomatous carcinoma, lymphoepithelial carcinoma, carcinoma mastitoides, carcinoma medullare, medullary carcinoma, carcinoma melanodes, melanotic carcinoma, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, carcinoma *nigrum*, oat cell carcinoma, carcinoma ossificans, osteoid carcinoma, ovarian carcinoma, papillary carcinoma, periportal carcinoma, pre-invasive carcinoma, prostate carcinoma, renal cell carcinoma of kidney (also called adenocarcinoma of kidney and hypemephoroid carcinoma), reserve cell carcinoma, carcinoma sarcomatodes, scheinderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, carcinoma vilosum. In preferred embodiments, the methods of the present disclosure are used to treat subjects having cancer of the breast, cervix, ovary, prostate, lung, colon and rectum, pancreas, stomach, or kidney.

Sarcomas are mesenchymal neoplasms that arise in bone and soft tissues. Different types of sarcomas are recognized and these include: liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extraskeletal (i.e., non-bone)

Ewing's sarcoma, and primitive neuroectodermal tumor [PNET]), synovial sarcoma, angiosarcomas, hemangiosarcomas, lymphangiosarcomas, Kaposi's sarcoma, hemangioendothelioma, fibrosarcoma, desmoid tumor (also called aggressive fibromatosis), dermatofibrosarcoma protuberans (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) (also known as GI stromal sarcoma), osteosarcoma (also known as osteogenic sarcoma)-skeletal and extraskeletal, and chondrosarcoma.

In some embodiments, the cancer to be treated can be a refractory cancer. A "refractory cancer," as used herein, is a cancer that is resistant to the standard of care prescribed. These cancers may appear initially responsive to a treatment (and then recur), or they may be completely non-responsive to the treatment. The ordinary standard of care will vary depending upon the cancer type, and the degree of progression in the subject. It may be a chemotherapy, or surgery, or radiation, or a combination thereof. Those of ordinary skill in the art are aware of such standards of care. Subjects being treated according to the present disclosure for a refractory cancer therefore may have already been exposed to another treatment for their cancer. Alternatively, if the cancer is likely to be refractory (e.g., given an analysis of the cancer cells or history of the subject), then the subject may not have already been exposed to another treatment. Examples of refractory cancers include, but are not limited to, leukemia, melanomas, renal cell carcinomas, colon cancer, liver (hepatic) cancers, pancreatic cancer, Non-Hodgkin's lymphoma and lung cancer.

Any of the immune cells expressing chimeric receptors described herein may be administered in a pharmaceutically acceptable carrier or excipient as a pharmaceutical composition.

The phrase "pharmaceutically acceptable," as used in connection with compositions and/or cells of the present disclosure, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans. "Acceptable" means that the carrier is compatible with the active ingredient of the composition (e.g., the nucleic acids, vectors, cells, or therapeutic antibodies) and does not negatively affect the subject to which the composition(s) are administered. Any of the pharmaceutical compositions and/or cells to be used in the present methods can comprise pharmaceutically acceptable carriers, excipients, or stabilizers in the form of lyophilized formations or aqueous solutions.

Pharmaceutically acceptable carriers, including buffers, are well known in the art, and may comprise phosphate, citrate, and other organic acids; antioxidants including ascorbic acid and methionine; preservatives; low molecular weight polypeptides; proteins, such as serum albumin, gelatin, or immunoglobulins; amino acids; hydrophobic polymers; monosaccharides; disaccharides; and other carbohydrates; metal complexes; and/or non-ionic surfactants. Sec, e.g. Remington: *The Science and Practice of Pharmacy* 20th Ed. (2000) Lippincott Williams and Wilkins, Ed. K. E. Hoover.

Kits for Therapeutic Uses

Also within the scope of the present disclosure are kits for use of the present agents/compositions. Such kits may include one or more containers comprising a first pharmaceutical composition that comprises at least one monoterpene or sesquiterpene, and a pharmaceutically acceptable carrier, and a second pharmaceutical composition that comprises at least one therapeutic agent and a pharmaceutically acceptable carrier. In another embodiment, the kit may include one or more containers comprising a pharmaceutical composition that comprises at least one monoterpene or sesquiterpene, at least one therapeutic agent, and a pharmaceutically acceptable carrier.

In some embodiments, the kit can comprise instructions for use in any of the methods described herein. The included instructions can comprise a description of administration of the first and second pharmaceutical compositions to a subject to achieve the intended activity in a subject. The kit may further comprise a description of selecting a subject suitable for treatment based on identifying whether the subject is in need of the treatment. In some embodiments, the instructions comprise a description of administering the pharmaceutical compositions to a subject who is in need of the treatment.

The instructions relating to the use of the pharmaceutical compositions described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert. The label or package insert indicates that the pharmaceutical compositions are used for treating, delaying the onset, and/or alleviating a disease or disorder in a subject.

The kits provided herein are in suitable packaging. Suitable packaging includes, but is not limited to, vials, bottles, jars, flexible packaging, and the like. Also contemplated are packages for use in combination with a specific device, such as an inhaler, nasal administration device, or an infusion device. A kit may have a sterile access port (for example, the container may be an intravenous solution bag or a vial having a stopper pierceable by a hypodermic injection needle). The container may also have a sterile access port.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

Perillyl alcohol derivatives include, perillyl alcohol esters, perillic aldehyde, dihydroperillic acid, and perillic acid. The derivatives of perillyl alcohol may also include its oxidative and nucleophilic/electrophilic addition derivatives. U.S. Patent Publication No. 20090031455. U.S. Pat. Nos. 6,133,324 and 3,957,856.

The invention also provides for methods of using monoterpenes (or sesquiterpenes) and at least one therapeutic agent to treat a disease, such as cancer or other nervous system disorders. Monoterpenes (or sesquiterpenes) may be administered alone, or in combination with the therapeutic agent. The monoterpene or sesquiterpene may also be co-administered with the therapeutic agent. Monoterpenes (or sesquiterpenes) can be administered in combination with the therapeutic agent. The agents may be administered concurrently or sequentially. Monoterpenes (or sesquiterpenes) can be administered before, during or after the administration of the therapeutic agent.

The monoterpenes (or sesquiterpenes) may be used as a solvent or a permeation enhancer to deliver a therapeutic agent to the lesion site. For example, monoterpenes (or sesquiterpenes) may be used as a solvent or a permeation enhancer to deliver chemotherapeutic agents to tumor cells. The monoterpene or sesquiterpene may also be used as a solvent for vaccines, which may be delivered through any suitable route.

The present compositions and methods may be used for the treatment of nervous system cancers, such as a malignant glioma (e.g., astrocytoma, anaplastic astrocytoma, glioblastoma multiforme), retinoblastoma, pilocytic astrocytomas (grade I), meningiomas, metastatic brain tumors, neuroblastoma, pituitary adenomas, skull base meningiomas, and skull base cancer. As used herein, the term "nervous system tumors" refers to a condition in which a subject has a malignant proliferation of nervous system cells.

Cancers that can be treated by the present compositions and methods include, but are not limited to, lung cancer, car, nose and throat cancer, leukemia, colon cancer, melanoma, pancreatic cancer, mammary cancer, prostate cancer, breast cancer, hematopoietic cancer, ovarian cancer, basal cell carcinoma, biliary tract cancer; bladder cancer; bone cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia including acute myeloid leukemia, acute lymphoid leukemia, chronic myeloid leukemia, chronic lymphoid leukemia; liver cancer; lymphoma including Hodgkin's and Non-Hodgkin's lymphoma; myeloma; fibroma, neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas. U.S. Pat. No. 7,601,355.

The present invention also provides methods and compositions for treating CNS disorders, including, without limitation, primary degenerative neurological disorders such as Alzheimer's, Parkinson's, psychological disorders, psychosis, and depression.

The present compositions may be used in combination with radiation therapy.

The present monoterpene or sesquiterpene may be used in combination with at least one therapeutic agents, including, but not limited to, chemotherapeutic agents, immunotherapeutic agents, and antibodies (e.g., monoclonal antibodies). The anti-cancer agents that may be used in combination with the purified monoterpene or sesquiterpene can have one or more of the following effects on cancer cells or the subject: cell death; decreased cell proliferation; decreased numbers of cells; inhibition of cell growth; apoptosis; necrosis; mitotic catastrophe; cell cycle arrest; decreased cell size; decreased cell division; decreased cell survival; decreased cell metabolism; markers of cell damage or cytotoxicity; indirect indicators of cell damage or cytotoxicity such as tumor shrinkage; improved survival of a subject; or disappearance of markers associated with undesirable, unwanted, or aberrant cell proliferation. U.S. Patent Publication No. 20080275057.

Also encompassed by the present invention are admixtures and/or coformulations of a monoterpene (or sesquiterpene) and at least one therapeutic agent, including, but not limited to, a chemotherapeutic agent.

Chemotherapeutic agents include, but are not limited to, DNA alkylating agents, topoisomerase inhibitors, endoplasmic reticulum stress inducing agents, a platinum compound, an antimetabolite, vincalkaloids, taxanes, epothilones, enzyme inhibitors, receptor antagonists, therapeutic antibodies, tyrosine kinase inhibitors, boron radiosensitizers (i.e. velcade), and chemotherapeutic combination therapies.

DNA alkylating agents are well known in the art and are used to treat a variety of tumors. Non-limiting examples of DNA alkylating agents are nitrogen mustards, such as Mechlorethamine, Cyclophosphamide (Ifosfamide, Trofosfamide), Chlorambucil (Melphalan, Prednimustine), Bendamustine, Uramustine and Estramustine; nitrosoureas, such as Carmustine (BCNU), Lomustine (Semustine), Fotemustine, Nimustine, Ranimustine and Streptozocin; alkyl sulfonates, such as Busulfan (Mannosulfan, Treosulfan); Aziridines, such as Carboquone, ThioTEPA, Triaziquone, Triethylenemelamine; Hydrazines (Procarbazine); Triazenes such as Dacarbazine and Temozolomide; Altretamine and Mitobronitol.

Non-limiting examples of Topoisomerase I inhibitors include Campothecin derivatives including CPT-11 (irinotecan), SN-38, APC, NPC, campothecin, topotecan, exatecan mesylate, 9-nitrocamptothecin, 9-aminocamptothecin, lurtotecan, rubitecan, silatecan, gimatecan, diflomotecan, extatecan, BN-80927, DX-8951f, and MAG-CPT as described in Pommier Y. (2006) *Nat. Rev. Cancer* 6 (10): 789-802 and U.S. Patent Publication No. 200510250854; Protoberberine alkaloids and derivatives thereof including berberrubine and coralyne as described in Li et al. (2000) *Biochemistry* 39 (24): 7107-7116 and Gatto et al. (1996) *Cancer Res.* 15 (12): 2795-2800; Phenanthroline derivatives including Benzo[i]phenanthridine, Nitidine, and fagaronine as described in Makhey et al. (2003) *Bioorg. Med. Chem.* 11 (8): 1809-1820; Terbenzimidazole and derivatives thereof as described in Xu (1998) *Biochemistry* 37 (10): 3558-3566; and Anthracycline derivatives including Doxorubicin, Daunorubicin, and Mitoxantrone as described in Foglesong et al. (1992) *Cancer Chemother. Pharmacol.* 30 (2): 123-125, Crow et al. (1994) *J. Med. Chem.* 37 (19): 31913194, and Crespi et al. (1986) *Biochem. Biophys. Res. Commun.* 136 (2): 521-8. Topoisomerase II inhibitors include, but are not limited to Etoposide and Teniposide. Dual topoisomerase I and II inhibitors include, but are not limited to, Saintopin and other Naphthecenediones, DACA and other Acridine-4-Carboxamindes, Intoplicine and other Benzopyridoindoles, TAS-103 and other 7H-indeno[2,1-c]Quinoline-7-ones, Pyrazoloacridine, XR 11576 and other Benzophenazines, XR 5944 and other Dimeric compounds, 7-oxo-7H-dibenz[f,ij]Isoquinolines and 7-oxo-7H-benzo[e]Perimidines, and Anthracenyl-amino Acid Conjugates as described in Denny and Baguley (2003) *Curr. Top. Med. Chem.* 3 (3): 339-353. Some agents inhibit Topoisomerase II and have DNA intercalation activity such as, but not limited to, Anthracyclines (Aclarubicin, Daunorubicin, Doxorubicin, Epirubicin, Idarubicin, Amrubicin, Pirarubicin, Valrubicin, Zorubicin) and Antracenediones (Mitoxantrone and Pixantrone).

Examples of endoplasmic reticulum stress inducing agents include, but are not limited to, dimethyl-celecoxib (DMC), nelfinavir, celecoxib, and boron radiosensitizers (i.e. velcade (Bortezomib)).

Platinum based compound which is a subclass of DNA alkylating agents. Non-limiting examples of such agents include Carboplatin, Cisplatin, Nedaplatin, Oxaliplatin, Triplatin tetranitrate, Satraplatin, Aroplatin, Lobaplatin, and JM-216. (see McKeage et al. (1997) *J. Clin. Oncol.* 201:

1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

Non-limiting examples of antimetabolite agents include Folic acid based, i.e. dihydrofolate reductase inhibitors, such as Aminopterin, Methotrexate and Pemetrexed; thymidylate synthase inhibitors, such as Raltitrexed, Pemetrexed; Purine based, i.e. an adenosine deaminase inhibitor, such as Pentostatin, a thiopurine, such as Thioguanine and Mercaptopurine, a halogenated/ribonucleotide reductase inhibitor, such as Cladribine, Clofarabine, Fludarabine, or a guanine/guanosine: thiopurine, such as Thioguanine; or Pyrimidine based, i.e. cytosine/cytidine: hypomethylating agent, such as Azacitidine and Decitabine, a DNA polymerase inhibitor, such as Cytarabine, a ribonucleotide reductase inhibitor, such as Gemcitabine, or a thymine/thymidine: thymidylate synthase inhibitor, such as a Fluorouracil (5-FU). Equivalents to 5-FU include prodrugs, analogs and derivative thereof such as 5'-deoxy-5-fluorouridine (doxifluroidine), 1-tetrahydrofuranyl-5-fluorouracil (ftorafur), Capecitabine (Xeloda), S-I (MBMS-247616, consisting of tegafur and two modulators, a 5-chloro-2,4dihydroxypyridine and potassium oxonate), ralititrexed (tomudex), nolatrexed (Thymitaq, AG337), LY231514 and ZD9331, as described for example in Papamicheal (1999) The Oncologist 4:478-487.

Examples of vincalkaloids, include, but are not limited to Vinblastine, Vincristine, Vinflunine, Vindesine and Vinorelbine.

Examples of taxanes include, but are not limited to docetaxel, Larotaxel, Ortataxel, Paclitaxel and Tesetaxel. An example of an epothilone is iabepilone.

Examples of enzyme inhibitors include, but are not limited to farnesyltransferase inhibitors (Tipifamib); CDK inhibitor (Alvocidib, Seliciclib); proteasome inhibitor (Bortezomib); phosphodiesterase inhibitor (Anagrelide; rolipram); IMP dehydrogenase inhibitor (Tiazofurine); and lipoxygenase inhibitor (Masoprocol). Examples of receptor antagonists include but are not limited to ERA (Atrasentan); retinoid X receptor (Bexarotene); and a sex steroid (Testolactone).

Examples of therapeutic antibodies include but are not limited to anti-HER1/EGFR (Cetuximab, Panitumumab); Anti-HER2/neu (erbB2) receptor (Trastuzumab); Anti-EpCAM (Catumaxomab, Edrecolomab) Anti-VEGF-A (Bevacizumab); Anti-CD20 (Rituximab, Tositumomab, Ibritumomab); Anti-CD52 (Alemtuzumab); and Anti-CD33 (Gemtuzumab). U.S. Pat. Nos. 5,776,427 and 7,601,355.

Examples of tyrosine kinase inhibitors include, but are not limited to inhibitors to ErbB: HER1/EGFR (Erlotinib, Gefitinib, Lapatinib, Vandetanib, Sunitinib, Neratinib); HER2/neu (Lapatinib, Neratinib); RTK class III: C-kit (Axitinib, Sunitinib, Sorafenib), FLT3 (Lestaurtinib), PDGFR (Axitinib, Sunitinib, Sorafenib); and VEGFR (Vandetanib, Semaxanib, Cediranib, Axitinib, Sorafenib); bcr-abl (Imatinib, Nilotinib, Dasatinib); Src (Bosutinib) and Janus kinase 2 (Lestaurtinib).

Cetuximab is an example of an anti-EGFR antibody. It is a chimeric human/mouse monoclonal antibody that targets the epidermal growth factor receptor (EGFR). Biological equivalent antibodies are identified herein as modified antibodies and those which bind to the same epitope of the EGFR antigen and produce a substantially equivalent biological response such as, preventing ligand binding of the EGFR, preventing activation of the EGFR receptor and the blocking of the downstream signaling of the EGFR pathway resulting in disrupted cell growth.

"Lapatinib" (Tykerb®) is a dual EGFR and erbB-2 inhibitor. Lapatinib has been investigated as an anticancer monotherapy, as well as in combination with trastuzumab, capecitabine, letrozole, paclitaxel and FOLFIR 1 (irinotecan, 5-fluorouracil and leucovorin), in a number of clinical trials. It is currently in phase III testing for the oral treatment of metastatic breast, head and neck, lung, gastric, renal and bladder cancer. A chemical equivalent of lapatinib is a small molecule or compound that is a tyrosine kinase inhibitor (TKI) or alternatively a HER-1 inhibitor or a HER-2 inhibitor. Several TKIs have been found to have effective antitumor activity and have been approved or are in clinical trials. Examples of such include, but are not limited to Zactima (ZD6474), Iressa (gefitinib) and Tarceva (erlotinib), imatinib mesylate (STI571; Gleevec), erlotinib (OSI-1774; Tarceva), canertinib (CI 1033), semaxinib (SU5416), vatalanib (PTK787/ZK222584), sorafenib (BAY 43-9006), sutent (*SUI* 1248) and lefltmomide (SU101). A biological equivalent of lapatinib is a peptide, antibody or antibody derivative thereof that is a HER-1 inhibitor and/or a HER-2 inhibitor. Examples of such include but are not limited to the humanized antibody trastuzumab and Herceptin.

PTK/ZK is a "small" molecule tyrosine kinase inhibitor with broad specificity that targets all VEGF receptors (VEGFR), the platelet-derived growth factor (PDGF) receptor, c-KIT and c-Fms. Drevs (2003) Idrugs 6 (8): 787-794. PTK/ZK is a targeted drug that blocks angiogenesis and lymphangiogenesis by inhibiting the activity of all known receptors that bind VEGF including VEGFR-I (Flt-1), VEGFR-2 (KDR/Flk-1) and VEGFR-3 (Flt-4). The chemical names of PTK/ZK are 1-[4-Chloroanilino]-4-[4-pyridylmethyl]phthalazine Succinate or 1-Phthalazinamine, N-(4-chlorophenyl)-4-(4-pyridinylmethyl)-butanedioate (1:1). Synonyms and analogs of PTK/TK are known as Vatalanib, CGP79787D, PTK787/ZK 222584, CGP-79787, DE-00268, PTK-787, PTK787A, VEGFR-TK inhibitor, ZK 222584 and ZK.

Chemotherapeutic agents that can be used in combination with the monoterpenes or sesquiterpenes may also include amsacrine, Trabectedin, retinoids (Alitretinoin, Tretinoin), Arsenic trioxide, asparagine depleter Asparaginase/Pegaspargase), Celecoxib, Demecolcine, Elesclomol, Elsamitrucin, Etoglucid, Lonidamine, Lucanthone, Mitoguazone, Mitotane, Oblimersen, Temsirolimus, and Vorinostat.

Other therapeutic agents which may be used with the compositions and methods of the present invention, include, for example, CAR-T cells, CAR-macrophages or CAR-NK cells.

The present compositions and methods may be used to increase paracellular permeability, for example, paracellular permeability of endothelial cells or epithelial cells. The present compositions and methods may be used to increase blood brain barrier permeability. The effects of administration on the permeability of the blood brain barrier may last for between 5 minutes and 10 hours; other ranges, include, at least about 15 minutes, 30 minutes, 1 hour, 2 hours, 3 hours, 5 hours, 10 hours, 24 hours, 48 hours, or 72 hours.

The present compositions and methods may be used to decrease or inhibit angiogenesis. The present compositions and methods may decrease or inhibit production of pro-angiogenic cytokines, including, but not limited to, vascular endothelial growth factor (VEGF) and interleukin 8 (IL8).

The monoterpenes or sesquiterpenes may be used in combination with angiogenesis inhibitors. Examples of angiogenesis inhibitors include, but are not limited to, angiostatin, angiozyme, antithrombin III, AG3340, VEGF inhibitors (e.g., anti-VEGF antibody), batimastat, bevacizumab (avastin), BMS-275291, CAI, 2C3, HuMV833 Canstatin, Captopril, carboxyamidotriazole, cartilage derived inhibitor (CDI), CC-5013, 6-O-(chloroacetyl-carbonyl)-fumagillol, COL-3, combretastatin, combretastatin A4 Phosphate, Dalteparin, EMD 121974 (Cilengitide), endostatin, erlotinib, gefitinib (Iressa), genistein, halofuginone hydrobromide, Id1, Id3, IM862, imatinib mesylate, IMC-IC11 Inducible protein 10, interferon-alpha, interleukin 12, lavendustin A, LY317615 or AE-941, marimastat, mspin, medroxprogesterone acetate, Meth-1, Meth-2,2-methoxyestradiol (2-ME), ncovastat, otcopontin cleaved product, PEX, pgment epithelium growth factor (PEGF), platelet factor 4, prolactin fragment, proliferin-related protein (PRP), PTK787/ZK 222584, ZD6474, recombinant human platelet factor 4 (rPF4), restin, squalamine, SU5416, SU6668, SU11248 suramin, Taxol, Tecogalan, thalidomide, thrombospondin, TNP-470, troponin-1, vasostatin, VEG1, VEGF-Trap, and ZD6474.

Non-limiting examples of angiogenesis inhibitors also include, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, pentosan polysulfate, angiotensin II antagonists, cyclooxygenase inhibitors (including non-steroidal anti-inflammatory drugs (NSAIDs) such as aspirin and ibuprofen, as well as selective cyclooxygenase-2 inhibitors such as celecoxib and rofecoxib), and steroidal anti-inflammatories (such as corticosteroids, mineralocorticoids, dexamethasone, prednisone, prednisolone, methylpred, betamethasone).

Other therapeutic agents that modulate or inhibit angiogenesis and may also be used in combination with monoterpenes or sesquiterpenes include agents that modulate or inhibit the coagulation and fibrinolysis systems. Examples of such agents that modulate or inhibit the coagulation and fibrinolysis pathways include, but are not limited to, heparin, low molecular weight heparins and carboxypeptidase U inhibitors (also known as inhibitors of active thrombin activatable fibrinolysis inhibitor [TAFIa]). U.S. Patent Publication No. 20090328239. U.S. Pat. No. 7,638,549.

Immunomodulatory agents include, but are not limited to, cytokines, such interleukins, lymphokines, monokines, interfereons and chemokines.

Other permeation enhancers that may be used together with the monoterpene (or sesquiterpene) include, but are not limited to, fatty acid esters of glycerin, such as capric, caprylic, dodecyl, oleic acids; fatty acid esters of isosorbide, sucrose, polyethylene glycol; caproyllactylic acid; laureth-2; laureth-2 acetate; laureth-2 benzoate; laureth-3 carboxylic acid; laureth-4; laureth-5 carboxylic acid; oleth-2; glyceryl pyroglutamate oleate; glyceryl oleate; N-lauroyl sarcosine; N-myristoyl sarcosine; Noctyl-2-pyrrolidone; lauraminopropionic acid; polypropylene glycol-4-laureth-2; polypropylene glycol-4-laureth-5dimethyl lauramide; lauramide diethanolamine (DEA), lauryl pyroglutamate (LP), glyceryl monolaurate (GML), glyceryl monocaprylate, glyceryl monocaprate, glyceryl monooleate (GMO) and sorbitan monolaurate. Polyols or ethanol may act as a permeation enhancer or co-solvent. See U.S. Pat. Nos. 5,785,991; 5,843, 468; 5,882,676; and 6,004,578 for additional permeation enhancers.

Co-solvents are well-known in the art and include, without limitation, glycerol, polyethylene glycol (PEG), glycol, ethanol, methanol, propanol, isopropanol, butanol and the like.

The present composition may be administered by any method known in the art, including, without limitation, intraarterial, intranasal, oral, ocular, intraperitoneal, inhalation, intravenous, intracardiac injection (IC), intracerebroventricular (ICV), intracisternal injection or infusion, subcutaneous, implant, vaginal, sublingual, urethral (e.g., urethral suppository), subcutaneous, intramuscular, intravenous, transdermal, rectal, sub-lingual, mucosal, ophthalmic, spinal, intrathecal, intra-articular, intra-arterial, sub-arachinoid, bronchial and lymphatic administration. Topical formulation may be in the form of gel, ointment, cream, aerosol, etc.; intranasal formulation can be delivered as a spray or in a drop; transdermal formulation may be administered via a transdermal patch or iontorphoresis; inhalation formulation can be delivered using a nebulizer or similar device. Compositions can also take the form of tablets, pills, capsules, semisolids, powders, sustained release formulations, solutions, suspensions, elixirs, aerosols, or any other appropriate compositions.

To prepare such pharmaceutical compositions, one or more of the monoterpenes (or sesquiterpenes) and/or at least one therapeutic agent may be mixed with a pharmaceutical acceptable carrier, adjuvant and/or excipient, according to conventional pharmaceutical compounding techniques. Pharmaceutically acceptable carriers that can be used in the present compositions encompass any of the standard pharmaceutical carriers, such as a phosphate buffered saline solution, water, and emulsions, such as an oil/water or water/oil emulsion, and various types of wetting agents. The compositions can additionally contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols. For examples of carriers, stabilizers and adjuvants, see *Remington's Pharmaceutical Sciences*, edited by E. W. Martin (Mack Publishing Company, 18th ed., 1990). The compositions also can include stabilizers and preservatives.

As used herein, the term "therapeutically effective amount" is an amount sufficient to treat a specified disorder or disease or alternatively to obtain a pharmacological response treating a disorder or disease. Methods of determining the most effective means and dosage of administration can vary with the composition used for therapy, the purpose of the therapy, the target cell being treated, and the subject being treated. Treatment dosages generally may be titrated to optimize safety and efficacy. Single or multiple administrations can be carried out with the dose level and pattern being selected by the treating physician. Suitable dosage formulations and methods of administering the agents can be readily determined by those of skill in the art. For example, the composition is administered at about 0.01 mg/kg to about 200 mg/kg, about 0.1 mg/kg to about 100 mg/kg, or about 0.5 mg/kg to about 50 mg/kg. When the compounds described herein are co-administered with another agent or therapy, the effective amount may be less than when the agent is used alone.

The present disclosure also provides the compositions as described above for intranasal administration. As such, the compositions can further comprise a permeation enhancer. Southall et al. Developments in Nasal Drug Delivery, 2000.

The present compositions may be administered intranasally in a liquid form such as a solution, an emulsion, a suspension, drops, or in a solid form such as a powder, gel, or ointment. Devices to deliver intranasal medications are well known in the art. Nasal drug delivery can be carried out using devices including, but not limited to, intranasal inhalers, intranasal spray devices, atomizers, nasal spray bottles, unit dose containers, pumps, droppers, squeeze bottles, nebulizers, metered dose inhalers (MDI), pressurized dose inhalers, insufflators, and bi-directional devices. The nasal delivery device can be metered to administer an accurate effective dosage amount to the nasal cavity. The nasal delivery device can be for single unit delivery or multiple unit delivery. In a specific example, the ViaNase Electronic Atomizer from Kurve Technology (Bethell, Washington) can be used in this invention (world wide web, kurvetech dot com). The compounds of the present invention may also be delivered through a tube, a catheter, a syringe, a packtail, a pledget, a nasal tampon or by submucosal infusion. U.S. Patent Publication Nos. 20090326275, 20090291894, 20090281522 and 20090317377.

The present compositions can be formulated as aerosols using standard procedures. The monoterpene (or sesquiterpene) and/or at least one therapeutic agent may be formulated with or without solvents, and formulated with or without carriers. The formulation may be a solution, or may be an aqueous emulsion with one or more surfactants. For example, an aerosol spray may be generated from pressurized container with a suitable propellant such as, dichlorodifluoromethane, trichlorofluoromethane, dichlorotetrafluoroethane, hydrocarbons, compressed air, nitrogen, carbon dioxide, or other suitable gas. The dosage unit can be determined by providing a valve to deliver a metered amount. Pump spray dispensers can dispense a metered dose or a dose having a specific particle or droplet size. As used herein, the term "aerosol" refers to a suspension of fine solid particles or liquid solution droplets in a gas. Specifically, aerosol includes a gas-borne suspension of droplets of a monoterpene (or sesquiterpene), as may be produced in any suitable device, such as an MDI, a nebulizer, or a mist sprayer. Aerosol also includes a dry powder composition of the composition of the instant invention suspended in air or other carrier gas. Gonda (1990) *Critical Reviews in Therapeutic Drug Carrier Systems* 6:273-313. Raeburn et al., (1992) *Pharmacol. Toxicol. Methods* 27:143-159.

The present compositions may be delivered to the nasal cavity as a powder in a form such as microspheres delivered by a nasal insufflator. The present compositions may be absorbed to a solid surface, for example, a carrier. The powder or microspheres may be administered in a dry, air-dispensable form. The powder or microspheres may be stored in a container of the insufflator. Alternatively, the powder or microspheres may be filled into a capsule, such as a gelatin capsule, or other single dose unit adapted for nasal administration.

The pharmaceutical composition can be delivered to the nasal cavity by direct placement of the composition in the nasal cavity, for example, in the form of a gel, an ointment, a nasal emulsion, a lotion, a cream, a nasal tampon, a dropper, or a bioadhesive strip. In certain embodiments, it can be desirable to prolong the residence time of the pharmaceutical composition in the nasal cavity, for example, to enhance absorption. Thus, the pharmaceutical composition can optionally be formulated with a bioadhesive polymer, a gum (e.g., xanthan gum), chitosan (e.g., highly purified cationic polysaccharide), pectin (or any carbohydrate that thickens like a gel or emulsifies when applied to nasal mucosa), a microsphere (e.g., starch, albumin, dextran, cyclodextrin), gelatin, a liposome, carbamer, polyvinyl alcohol, alginate, acacia, chitosans and/or cellulose (e.g., methyl or propyl; hydroxyl or carboxy; carboxymethyl or hydroxylpropyl).

The composition can be administered by oral inhalation into the respiratory tract, i.e., the lungs.

Typical delivery systems for inhalable agents include nebulizer inhalers, dry powder inhalers (DPI), and metered-dose inhalers (MDI).

Nebulizer devices produce a stream of high velocity air that causes a therapeutic agent in the form of liquid to spray as a mist. The therapeutic agent is formulated in a liquid form such as a solution or a suspension of particles of suitable size. In one embodiment, the particles are micronized. The term "micronized" is defined as having about 90% or more of the particles with a diameter of less than about 10 µm. Suitable nebulizer devices are provided commercially, for example, by PARI GmbH (Starnberg, Germany). Other nebulizer devices include Respimat (Bochringer Ingelheim) and those disclosed in, for example, U.S. Pat. Nos. 7,568,480 and 6,123,068, and WO 97/12687. The monoterpenes (or sesquiterpenes) can be formulated for use in a nebulizer device as an aqueous solution or as a liquid suspension.

DPI devices typically administer a therapeutic agent in the form of a free flowing powder that can be dispersed in a patient's air-stream during inspiration. DPI devices which use an external energy source may also be used in the present invention. In order to achieve a free flowing powder, the therapeutic agent can be formulated with a suitable excipient (e.g., lactose). A dry powder formulation can be made, for example, by combining dry lactose having a particle size between about 1 µm and 100 µm with micronized particles of the monoterpenes (or sesquiterpenes) and dry blending. Alternatively, the monoterpene can be formulated without excipients. The formulation is loaded into a dry powder dispenser, or into inhalation cartridges or capsules for use with a dry powder delivery device. Examples of DPI devices provided commercially include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (scc, e.g., U.S. Pat. No. 4,524,769); and Rotahaler (GlaxoSmithKline) (see, e.g., U.S. Pat. No. 4,353,365). Further examples of suitable DPI devices are described in U.S. Pat. Nos. 5,415,162, 5,239,993, and 5,715,810 and references therein.

MDI devices typically discharge a measured amount of therapeutic agent using compressed propellant gas. Formulations for MDI administration include a solution or suspension of active ingredient in a liquefied propellant. Examples of propellants include hydrofluoroalklanes (HFA), such as 1,1,1,2-tetrafluorocthane (HFA 134a) and 1,1,1,2,3,3,3-heptafluoro-n-propane, (HFA 227), and chlorofluorocarbons, such as CC13F. Additional components of HFA formulations for MDI administration include co-solvents, such as ethanol, pentane, water; and surfactants, such as sorbitan trioleate, oleic acid, lecithin, and glycerin. (See, for example, U.S. Pat. No. 5,225,183, EP 0717987, and WO 92/22286). The formulation is loaded into an aerosol canister, which forms a portion of an MDI device. Examples of MDI devices developed specifically for use with HFA propellants are provided in U.S. Pat. Nos. 6,006,745 and 6,143,227. For examples of processes of preparing suitable formulations and devices suitable for inhalation dosing see U.S. Pat. Nos. 6,268,533, 5,983,956, 5,874,063, and 6,221,398, and WO 99/53901, WO 00/61108, WO 99/55319 and WO 00/30614.

The monoterpenes (or sesquiterpenes) and/or at least one therapeutic agent may be encapsulated in liposomes or microcapsules for delivery via inhalation. A liposome is a vesicle composed of a lipid bilayer membrane and an aqueous interior. The lipid membrane may be made of phospholipids, examples of which include phosphatidylcholine such as lecithin and lysolecithin; acidic phospholipids such as phosphatidylserine and phosphatidylglycerol; and sphingophospholipids such as phosphatidylethanolamine and sphingomyelin. Alternatively, cholesterol may be added. A microcapsule is a particle coated with a coating material. For example, the coating material may consist of a mixture of a film-forming polymer, a hydrophobic plasticizer, a surface activating agent or/and a lubricant nitrogen-containing polymer. U.S. Pat. Nos. 6,313,176 and 7,563,768.

Because of their ability to easily penetrate the dermis, monoterpenes may also be used alone or in combination with at least one therapeutic agent via topical application. As a transdermal delivery agent, monoterpenes may also be used in combination with narcotics or analgesics for transdermal delivery of pain medication.

This invention also provides the compositions as described above for ocular administration. As such, the compositions can further comprise a permeation enhancer. For ocular administration, the compositions described herein can be formulated as a solution, emulsion, suspension, etc. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

The present compositions can be administered for a short or prolonged period of time. The present compositions can be administered to a mammal, preferably a human. Mammals include, but are not limited to, murines, rats, rabbit, simians, bovines, ovine, porcine, canines, feline, farm animals, sport animals, pets, equine, and primates.

The device for intranasal administration may be an intranasal spray device, an atomizer, a nebulizer, a metered dose inhaler (MDI), a pressurized dose inhaler, an insufflator, an intranasal inhaler, a nasal spray bottle, a unit dose container, a pump, a dropper, a squeeze bottle, or a bi-directional device.

The agents may be administered concurrently or sequentially.

The invention also provides a method for inhibiting the growth of a cell in vitro, ex vivo or in vivo, where a cell, such as a cancer cell, is contacted with an effective amount of the purified monoterpene (or sesquiterpene) as described herein. The present compositions and methods may be used to inhibit the growth of a cell that is resistant to a chemotherapeutic agent. For example, the present compositions and methods may be used to inhibit the growth of a temozolomide-resistant cell.

Pathological cells or tissue such as hyperproliferative cells or tissue may be treated by contacting the cells or tissue with an effective amount of the present composition. The cells, such as cancer cells, can be primary cancer cells or can be cultured cells available from tissue banks such as the American Type Culture Collection (ATCC). The pathological cells can be cells of a systemic cancer, gliomas, meningiomas, pituitary adenomas, or a CNS metastasis from a systemic cancer, lung cancer, prostate cancer, breast cancer, hematopoietic cancer or ovarian cancer. The cells can be from a vertebrate, preferably a mammal, more preferably a human. U.S. Patent Publication No. 2004/0087651. Balassiano et al. (2002) *Intern. J. Mol. Med.* 10:785-788. Thorne, et al. (2004) *Neuroscience* 127:481-496. Fernandes, et al. (2005) *Oncology Reports* 13:943-947. Da Fonseca, et al. (2008) *Surgical Neurology* 70:259267. Da Fonseca, et al. (2008) *Arch. Immunol. Ther. Exp.* 56:267-276. Hashizume, et al. (2008) *Neuroncology* 10:112-120.

Cancer stem cells (CSCs) or tumor initiating cells are immature cells with stem cell features such as self-renewal. However, self-renewal is exacerbated in CSCs. Reya et al., Stem cells, cancer, and cancer stem cells. *Nature*. 2001, 414 (6859): 105-11. Additionally, glioma CSCs are resistant to chemo- and radio-therapy. Bao et al., Glioma stem cells promote radioresistance by preferential activation of the DNA damage response. *Nature*. 2006, 444 (7120): 756-60. Rich et al., Chemotherapy and cancer stem cells. *Cell Stem Cell*. 2007; 1 (4): 353-5. The present compositions and methods may be used to inhibit the growth of a cancer stem cell, including, but not limited to, a glioblastoma cancer stem cell.

The following examples are presented for the purposes of illustration only and are not limiting the invention.

Example 1 NEO100—Mediated Human CAR T Cells Delivery to the Brain and Tumors

Preparation of Human CAR T Cells

The human CAR T cells (CD19 and Lym-1) were provided by Dr. Epstein (USC). Chimeric antigen receptors (CARs) are synthetic molecules containing 3 distinct modules: an extracellular antibody-based recognition site; a transmembrane module that anchors the molecule into the cell membrane; and a chimeric intracellular signaling domain that transmits the activation signal. Jensen et al., Designing chimeric antigen receptors to effectively and safely target tumors. Curr. Opin. Immunol. 2015, 33, 9-15. CAR T cells targeting CD19 have achieved impressive outcomes in the treatment of patients with relapsed or refractory (R/R) acute lymphoblastic leukemia (ALL). Ruella et al., Dual CD19 and CD123 targeting prevents antigen-loss relapses after CD19-directed immunotherapies. J. Clin. Invest. 2016, 126, (10), 3814-3826. Maude et al., CD19-targeted chimeric antigen receptor T-cell therapy for acute lymphoblastic leukemia. Blood 2015, 125, (26), 4017-23. Grupp et al., Durable Remissions in Children with Relapsed/Refractory ALL Treated with T Cells Engineered with a CD19-Targeted Chimeric Antigen Receptor (CTL019). Blood 2015, 126, (23), 681-681. Lym-1, a murine IgG2a monoclonal antibody, was generated by immunizing mice with nuclei isolated from Raji lymphoma cells. Epstein et al., Two new monoclonal antibodies, Lym-1 and Lym-2, reactive with human B-lymphocytes and derived tumors, with immunodiagnostic and immunotherapeutic potential. Cancer Res. 1987, 47, (3), 830-40. Lym-1 binds to a discontinuous conformational epitope on several HLA-DR subtypes with a greater binding affinity for malignant B cells than normal B cells. Rose et al., Critical Lym-1 binding residues on polymorphic HLA-DR molecules. Mol Immunol 1999, 36, (11-12), 789-97. As shown in FIG. 1, the schematic representation of Lym-1 CAR and CD19 (FMC 63) CAR constructs.

2-million CD19 and Lym-1 human CAR T cells that were suspended in 0.9% saline working solution to be used for the IV injection with and without intracardiac NEO100.

Intracardiac Puncture for NEO100

Preparation of the working solution for intracardiac injection of NEO100: 3% NEO100 suspended in 0.9% saline.

Standard Operating Procedures for Ultrasound Guided Intracardiac Puncture

Briefly, the animals were anesthetized using 2% isoflurane gas and fixed on the platform for intracardiac puncture. To penetrate the syringe needle into intercoastal space promptly through skin and muscle layers into the left ventricle under the guidance of ultrasound imaging.

An indication of successful insertion of the needle into the left ventricle is the reflux of fresh arterial blood (pink color in contrast to dark red venous blood) into the syringe. 40 μl 3% NEO100 in saline was injected slowly to complete intracardiac application. Direct cell injection into the heart could cause local microinfarctions if the cells are clumpy during injection, hemopericardium and death as a consequence. This is why ultrasound guided injections with a small 30G needle is important to minimize these potential adverse effects, (1) enabling the visualization of the needle tract to ensure that the needle enters the left ventricle only, and (2) subsequent monitoring of the heart through not only ECG but visualization of heart wall function after the injection. The fine gauge of the needle ensures that the cells are not clumpy when the cells are injected through intracardiac puncture.

Confirmation of Intracardiac Injection

An indication of successful insertion of the needle into the left ventricle is the reflux of fresh arterial blood (pink color in contrast to dark red venous blood) into the syringe.

Immediate after the completion of NEO100 injection, 2 million human CAR T cells in 40 μl PBS were injected through tail vein catheter that pre-primed with saline solution. To avoid the possible adverse effects mentioned above by direct cell injection through intracardiac application, we set up 2-step procedures for the study.

Step 1: 40 μl 3% NEO100 in saline was injected slowly to complete intracardiac application. This procedure allows NEO100 to exert the function of BBB disruption.

Step 2: 2-million CAR T cells were injected by IV through tail vein catheter.

Evaluation of CAR T Cell Spreading by IHC and Confocal Imaging

Brain Perfusion—In order to rule out the residue left over inside the blood vessel after euthanizing, the testing animals were perfused by 10 ml 0.9% normal saline solution through left ventricle to flush out the blood. Then, the brain was removed, buried in October, and stored in −80° C. for further analysis.

Confocal Imaging—8 μM fresh frozen sections were made by cryostasis machine and pasted on microslide. Coverslip was mounted on the brain section by DAPI mounting medium before Confocal examination.

IHC Staining—Standardized IHC staining procedures were adopted to detect the penetration of human CAR T cells inside the brain and the tumor formed (GL261 mouse glioma). The primary antibody, anti-Human CD3 antibody (CD38 (D7A6E™) XP® Rabbit mAb (#85061) (Cell Signaling, Boston, MA), was used to identify human derived CD3 positive cells (as shown in FIG. 2).

Study of Syngeneic Mouse Glioma Animal Model in C57 BL/6 Mice 100,000 GL261 mouse glioma cells were intracranially injected into immune competent C57 BL/6 mice. 3 weeks post tumor cell injection, mice with brain tumors were injected with 2 millions human CAR T cells (anti-CD19 and Lym-1) by intravenous application (IV), and combination of intracardiac (IC) with IV. The treated mice were euthanized 6 h post the interventions. For intracardiac application: 2-million anti-CD19 or Lym-1 CAR T cells given by IV injection after intracardiac injection of 3% NEO100 in PBS. For intravenous application: 2-million anti-CD19 or Lym-1 CAR T cells were suspended in 40 μl PBS injected through tail vein.

The brain was perfused with 0.9% saline solution, removed and stored at −80° C. for further analysis.

Antibodies applied for the testing include control antibody for negative staining: Rabbit (DA1E) mAb IgG Isotype, and antibody used to detect CD3 positive cells in vitro and in vivo: CD38 (D7A6E™) XP® Rabbit mAb (#85061).

CONCLUSION

No detectable CD3 positive cells were found in normal C57 BL/6 mouse brain.

Compared to conventional intravenously injection (IV), intracardiac injection of human CAR T cells (anti-CD19 and Lym-1) mediated by NEO100 can greatly increase the penetration into the tumor formed inside the brain.

3% NEO100 mediated intracardiac injection does not cause any severe adverse effect or animal death.

More CD3 positive cells were found in the normal parts of brain treated by intracardiac injection of NEO100, than that in IV injection only samples.

Example 2 Anti-Mouse PD-1 Antibody Mediated Therapeutic Efficacy in C57 BL/6 Mice Bearing Intracranial Syngeneic Mouse Glioma (GL261)

100,000 GL261 mouse glioma cells were injected intracranially to immune competent mice, C57 BL/6. 7 days post the injection, the mice were randomly divided into 4 experimental groups, and initiated the treatment at the same day.

Group 1. Control: IV and Intracardiac injection of 40 μl Saline Solution (5).

Group 2. Antibody treated mice: IV 40 μl Anti-mouse PD1 antibody at the dose of 2.5 mg/kg (5).

Group 3. NEO100 treated mice: Intracardiac injection of 40 μl 5% NEO100 (5).

Group 4. Combination of NEO100 and antibody treated mice: Intracardiac 40 μl 5% NEO100, followed by IV 40 μl Anti-PD1 antibody at the dose of 2.5 mg/kg (6).

Figure 3:
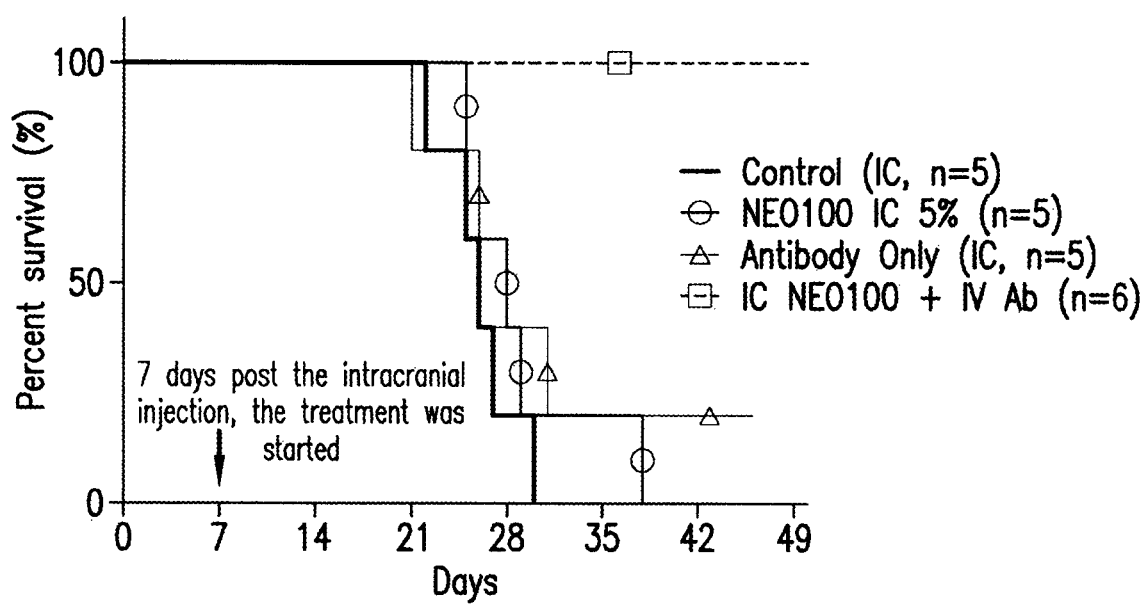
FIG. 3 shows the survival rates reflecting anti-mouse PD-1 antibody mediated therapeutic efficacy in C57 BL/6 bearing syngeneic mouse GBM (GL261) in the absence or presence of perillyl alcohol.
Figure 4A:
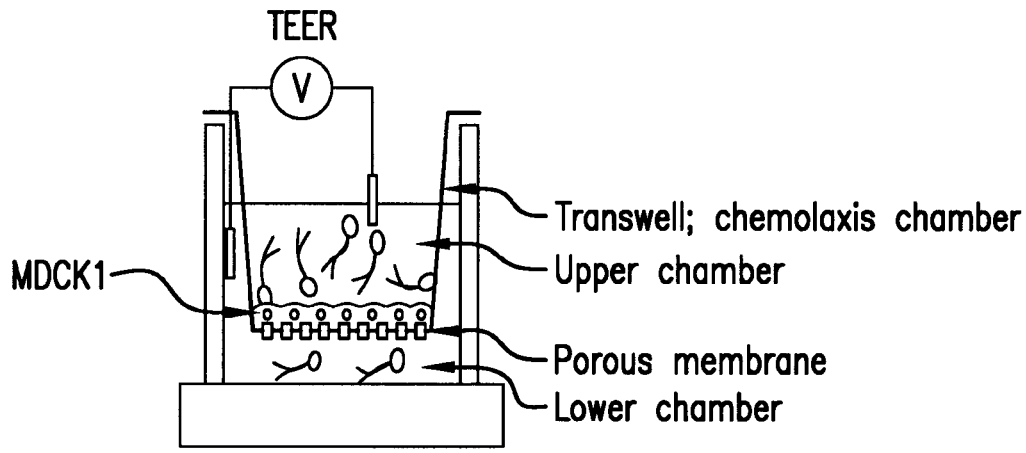
FIGS. 4A-4D show that NEO100 can be applied across an in vitro BBB model, and transiently allow labeled antibodies to cross it.
Figure 4B:
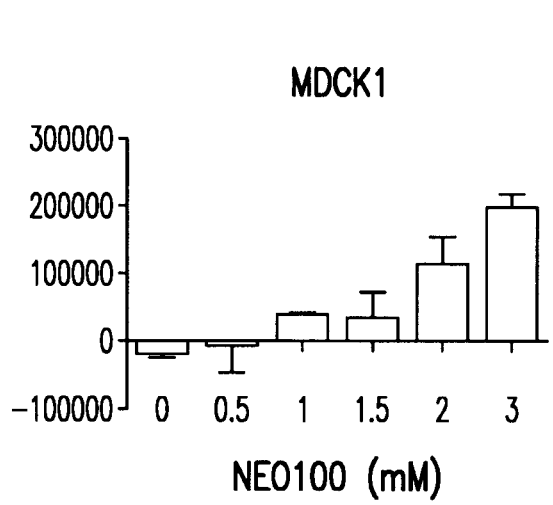
Figure 4C:
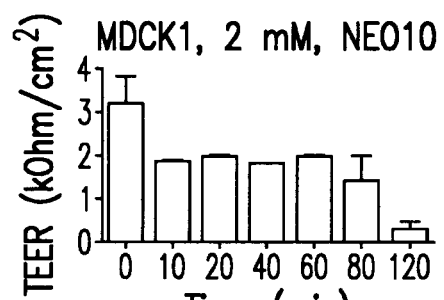
Figure 4D:
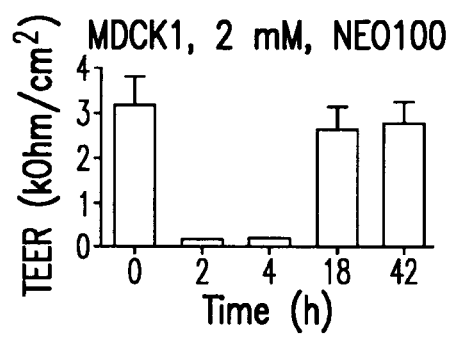

Results are shown in FIG. 3. We demonstrated that intracardiac injection of NEO100 (equivalent to intra-arterial injection for mice) could open the BBB for antibodies. We then performed a syngeneic model using mice GL26 glioma cells implanted intracranially. Mice were treated with saline, NEO100 alone, anti-PD1 intravenously alone, or NEO100 intracardiacally followed by anti-PD1 intravenously. All the mice treated with anti-PD1 intravenously in combination with NEO100 are still alive, while all the controls were dead except for one mice that received anti-PD1 intravenously.

Perillyl alcohol may be administered via the femoral artery (like cerebral angiography) using interventional neuroradiology.

Statistical Analysis

Animal survival data were plotted using the Kaplan-Meier method. One-way ANOVA was used for the overall test for differences. Grouped comparisons were performed using the Tukey method of adjusting for multiple comparisons. Logrank (Mantel-Cox) test was applied for the comparison of survival curves. A statistical evaluation result of $p<0.05$ was considered significant.

Control vs IC NEO100+IV Anti-mouse PD-1: ***
P<0.0003
Control vs IV Anti-mouse PD-1: ns, p=0.31
IV Anti-mouse PD-1 vs IC NEO100+IV Anti-mouse: **
P<0.005
Control vs IC NEO100: ns, p=0.397

Example 3

We demonstrated that NEO100 can be applied across an in vitro BBB model, and transiently allow labeled antibodies to transiently cross it (FIGS. 4A-4D).

Experiments were conducted to study whether perillyl alcohol (e.g., NEO100) can be used for intra-arterial delivery to transiently break down the BBB, allowing previously non-permeable small molecules or large molecules to penetrate to the brain.

Administration of perillyl alcohol (e.g., NEO100) may include intra-cardiac injection (intra-arterial injection in mice), and intravenous infusion.

Formulations include 10% NEO100 (27.5 ml Glycerol+ 27.5 ml Ethanol+3.0 ml NEO100).

Brain Perfusion-Before euthanizing, the testing animals was perfused by 0.9% normal saline solution through left ventricle. The brain was removed and buried in October, and stored in −80° C. for further analysis.

Ultrasound Guided Intracardiac Puncture-Briefly, the animals were anesthetized using 2% isoflurane gas and fixed on the platform for intracardiac puncture. To penetrate the syringe needle into intercoastal space promptly through skin and muscle layers into the left ventricle under the guidance of ultrasound imaging. An indication of successful insertion of the needle into the left ventricle is the reflux of fresh arterial blood (pink color in contrast to dark red venous blood) into the syringe.

Evans Blue is an Azo dye that has a very high affinity for serum albumin. The extravasation of stained albumin from circulation could be visualized.

Figure 5A:
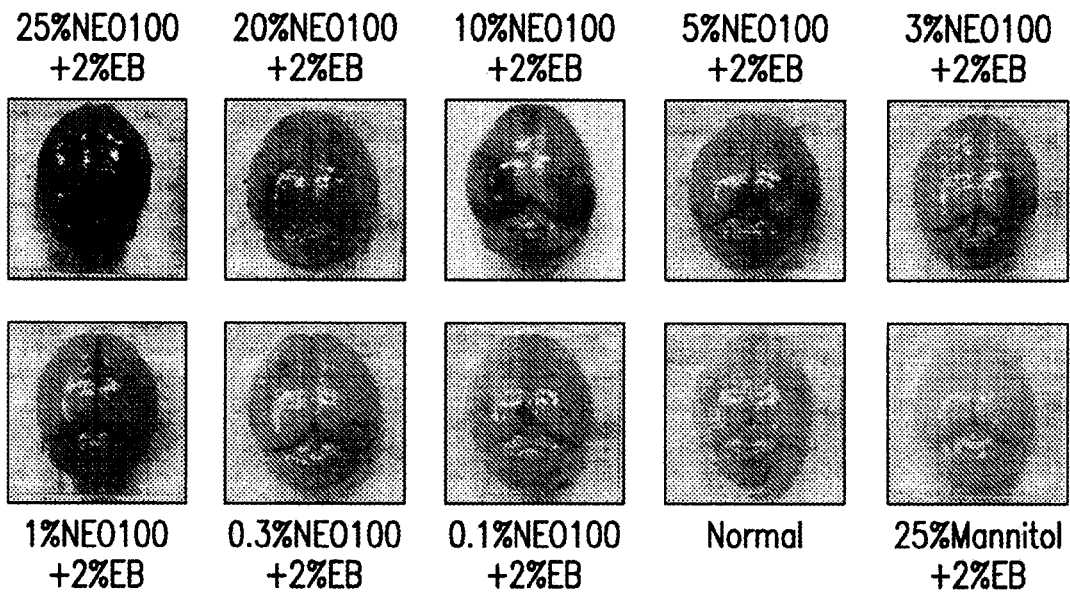
FIG. 5A shows intracardiac injection (IC) of mixtures of NEO100 (at different concentrations) and 2% Evan's Blue (EB).

NEO100 was delivered via intra-cardiac injection (left ventricle) to determine if there is increased uptake of Evans Blue, a BBB nonpermeable small molecule (dopamine), or antibodies into the brain. FIG. 5A shows intracardiac injection (IC) of mixtures of NEO100 and 2% Evan's Blue (EB). Different concentration of NE0100 (40 µl in 0.9% saline) was tested through intracardiac puncture, followed by immediate intravenous application of 2% Evans Blue (40 µl in volume). The brain was removed after perfusion. The results show that NEO100 at 1:1000 dilution (6.5 mM 40 µl) is still effective to disturb the BBB.

Figure 5B:
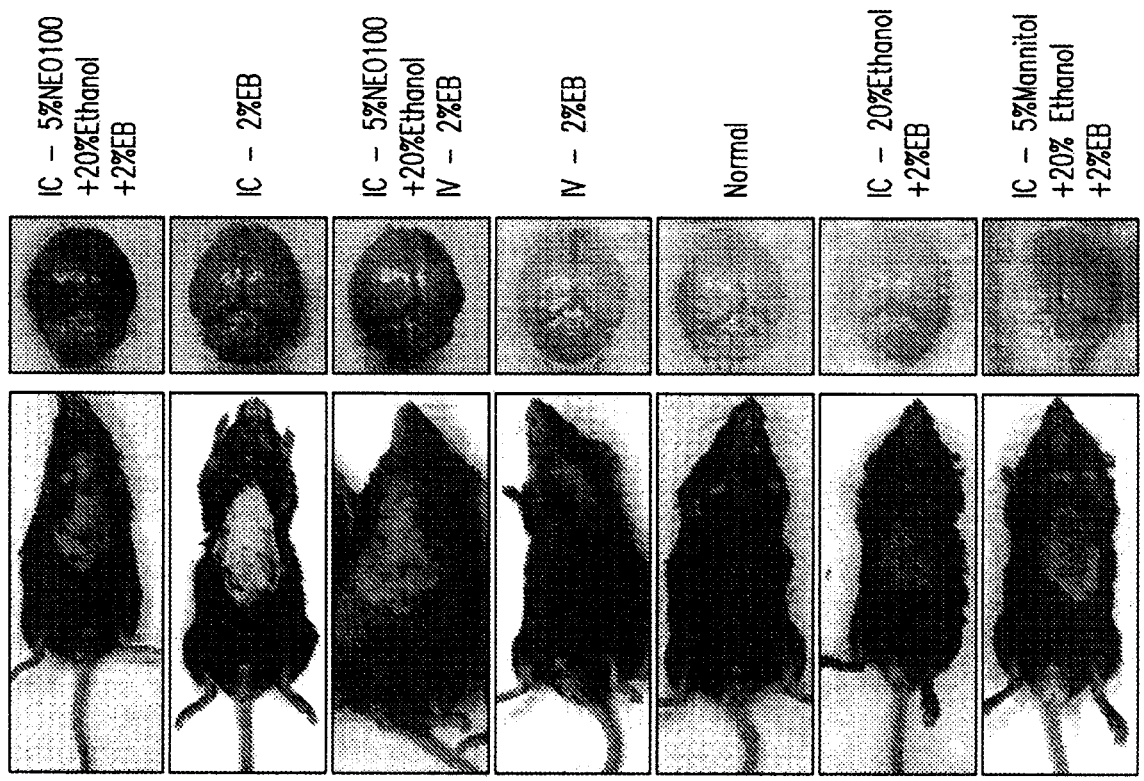
FIG. 5B shows EB penetration into brain after NEO100 applied by IC (intracardiac injection) or IV injection.

FIG. 5B shows EB penetration into brain after NEO100 applied by IC (intracardiac injection) or IV injection.

Figure 6:
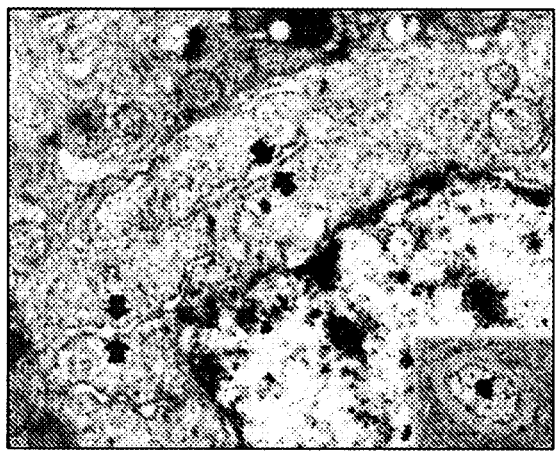
FIG. 6 shows NEO100 breached tight junctions in the brain.
Figure 6:
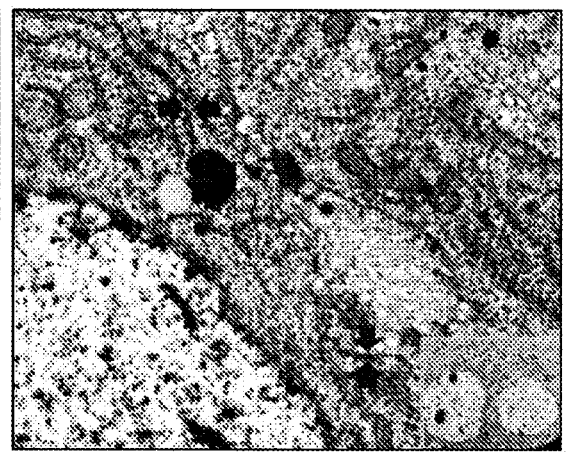
Figure 6:
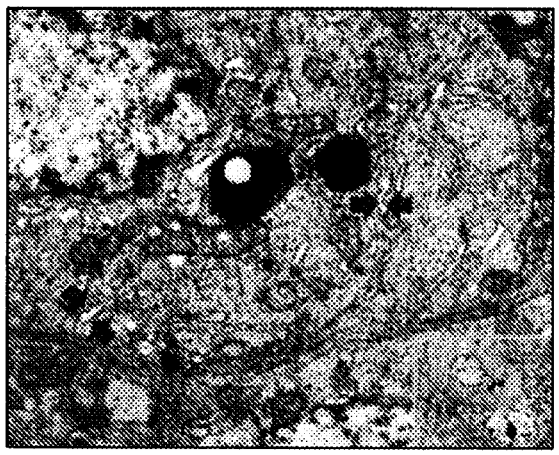
Figure 6:
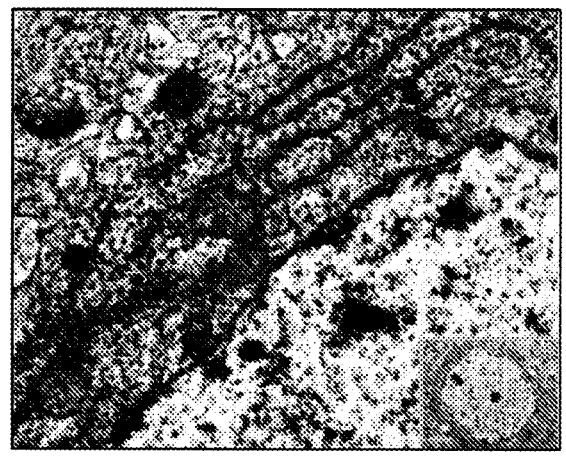

Experimental groups include:
IC 2% EB only
IC 20% ethanol+2% EB
IC 20% ethanol+2% EB+5% NEO100
IC 20% ethanol+5% NEO100, followed by 2% EB tail vein injection
IV 20% ethanol+2% EB+5% NEO100
IV 20% ethanol+2% EB FIG. 6 demonstrated that the tight junction has been breached dramatically in the brain treated with intracardiac injection of 5% NEO100 compared to that in normal brain.

Pharmacologic treatment of Parkinson's Disease (PD) is mainly symptomatic based on dopamine (DA) replacement therapy, as exogenous DA and other catecholamines cannot be administered due to their poor BBB penetration. Dopamine is a water-soluble hydrophilic drug that does not satisfy the characteristics of a substance that can enter the brain by BBB penetration.

Figure 7:
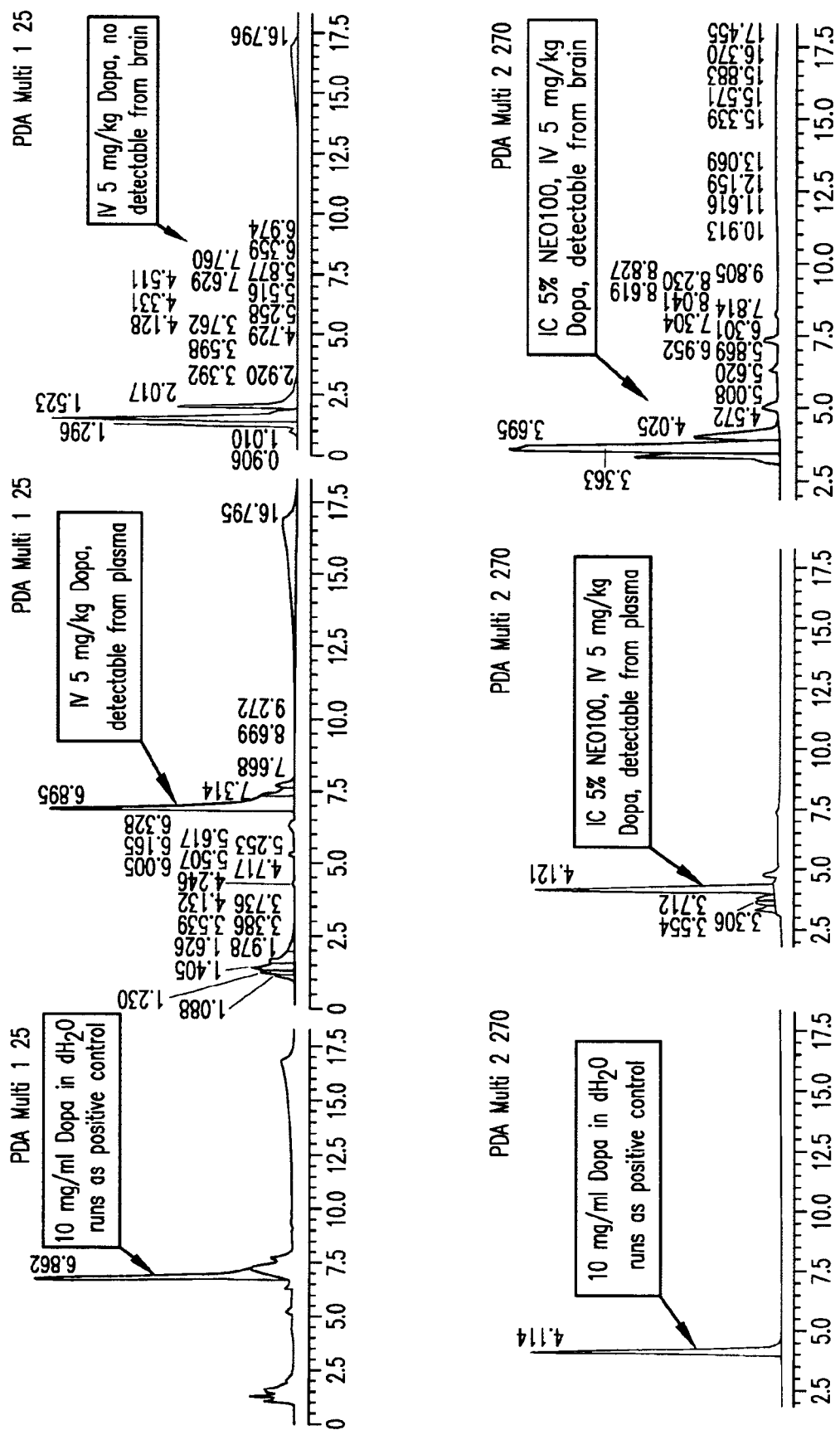
FIG. 7 shows NEO100 mediated dopamine delivery through the breached blood-brain-barrier.

FIG. 7 shows that NEO100 mediated dopamine delivery through the breached blood-brain-barrier.

Figure 8:
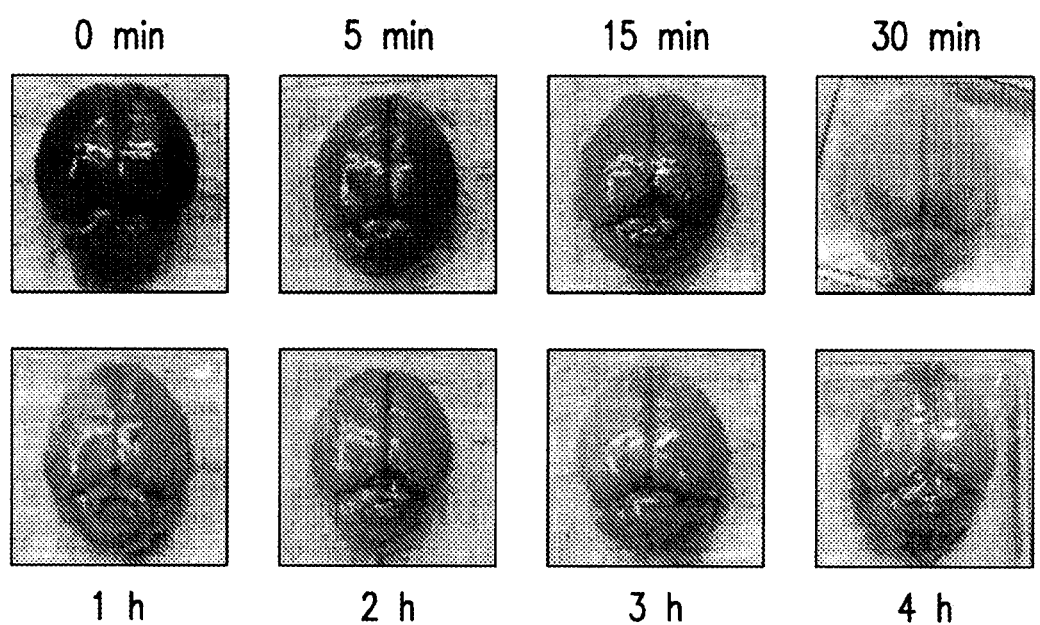
FIG. 8 shows measurement of BBB opening and closing time.

FIG. 8 shows the measurement of BBB opening and closing time. The immune competent C57 BL/6 mice was injected with 5% NEO100 (v/v) through intracardiac puncture (IC), followed by intravenous injection of 2% Evans Blue at different time points, such as 0, 5 min, 15 min, 30 min, 1-hour, 2-hour, 3-hour, and 4 hours, post the IC injection.

The experimental procedure included:
1. Intracardiac Injection (IC): 5% NEO100.
2. Followed by intravenous injection (IV) of 2% EB at different times.
3. The testing animals were euthanized one hour after the IV injection.

Figure 9:
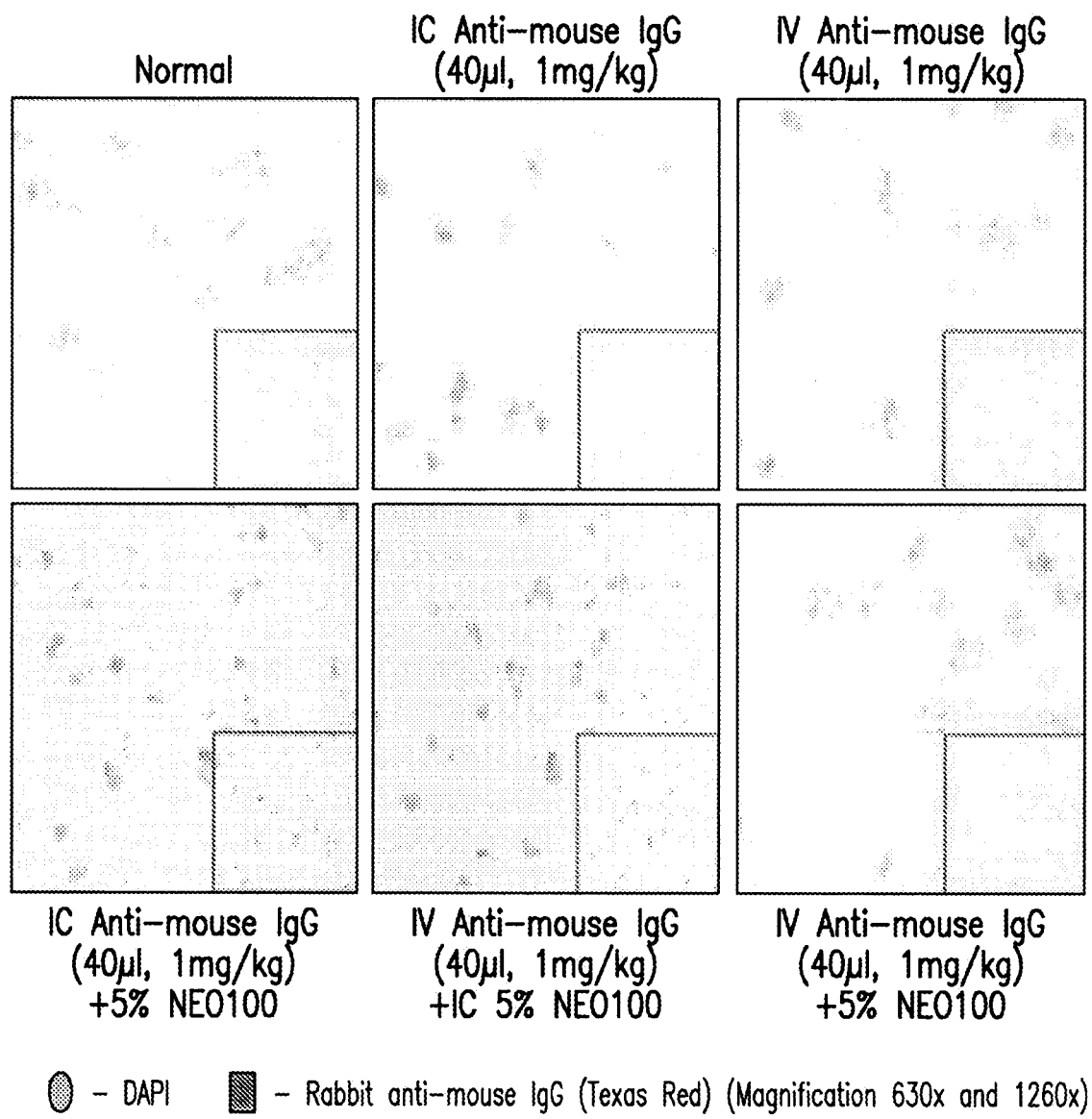
FIG. 9 shows anti-mouse IgG antibody delivery in the absence or presence of perillyl alcohol.

FIG. 9 shows anti-mouse IgG antibody (rabbit anti-mouse IgG H&L (Texas Red)-Ab6726) delivery in the absence or presence of perillyl alcohol.

Figure 10:
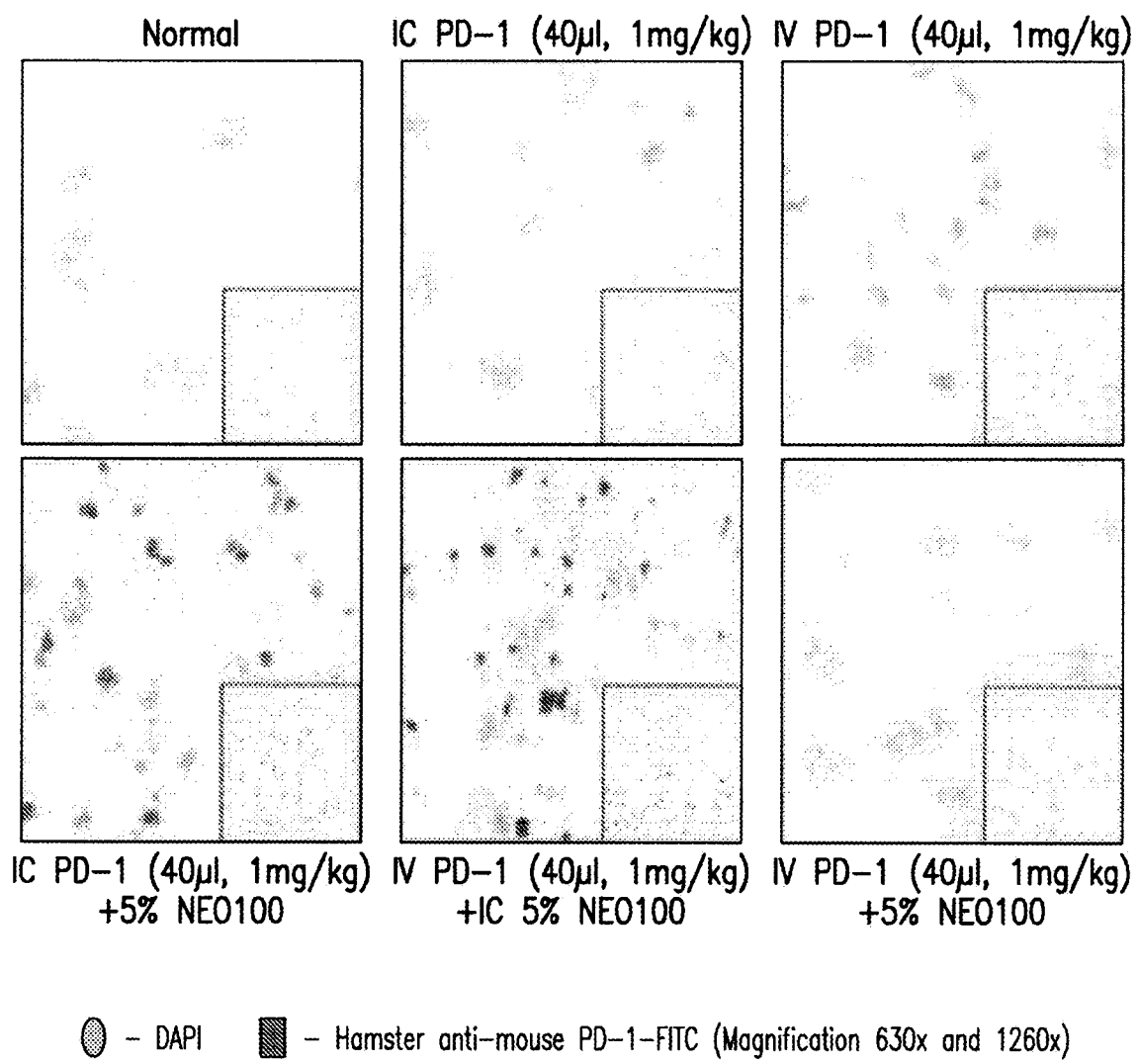
FIG. 10 shows anti-PD-1 antibody delivery in the absence or presence of perillyl alcohol.

FIG. 10 shows anti-PD-1 antibody (Armenian hamster anti-mouse CD279 (PD-1) monoclonal antibody (J43)) delivery in the absence or presence of perillyl alcohol. PD-L1 binds to PD-1 and inhibits T cell killing of tumor cells. Blocking PD-L1 or PD-1 allows T cell killing of tumor cells.

NEO100 is safe to administer intraarterially.

Figure 11:
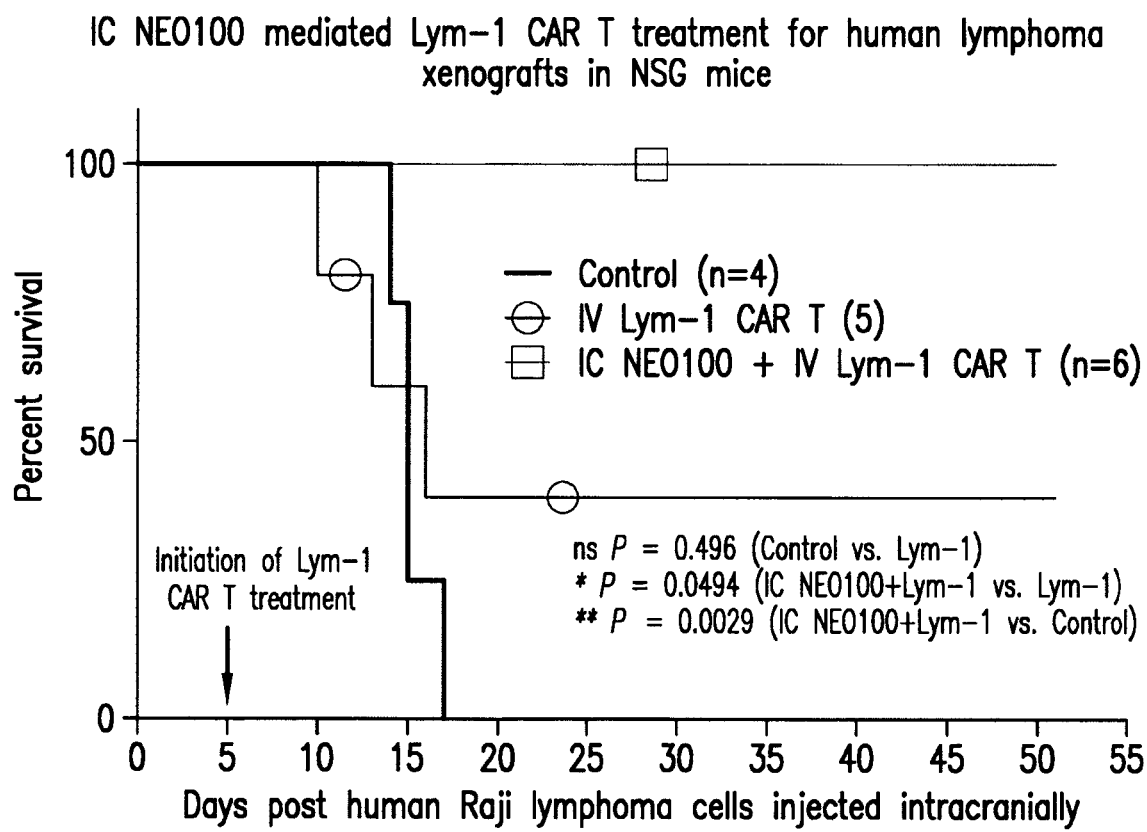
FIG. 11 shows a Kaplan Meier survival curve after NEO100 mediated human CAR T cells (Lym-1 CAR) delivery in the treatment of intracranial Raji lymphoma xenografts in NSG mice.

Example 4 NEO100 Mediated Human CAR T Cells (Lym-1 CAR) Delivery in the Treatment of Intracranial Raji Lymphoma Xenografts in NSG Mice (a) Intracranial lymphoma xenografts:
  50,000 ($5 \times 10^4$) human B-cell lymphoma cells, Raji's-Luc/GFP, were injected intracranially into NSG mice.
(b) Confirmation of the tumor uptake:
  5 days post the tumor cells injection, the optical imaging was performed to confirm the tumor uptake (100% tumor uptake).
(c) Initiation of CAR T infusion through tail vein catheter and intracardiac (IC) NEO100:
  There were 3 experimental groups: (1) Control; (2) IV CAR T ($5 \times 10e6$); (3) IV CAR T($5 \times 10e6$)+IC NEO100 (0.3% v/v=492 µM)
(d) Monitoring of NSG mice bearing IC lymphoma:
  Body weight was monitored for the physical condition of the mice during the treatment. Tumor growth was monitored by optical imaging.
(e) Animal Survival (Kaplan Meier Curve)
  As is evident from the survival curves (FIG. 11), the control mice, i.e., mice injected with the human B-cell lymphoma cells, died within 15-20 days after injection, whereas, mice injected with Lym-1 CAR T cells plus NEO100 survived (P=0.0029).

Example 5

POH will be placed into an intranasal inhaler (e.g., the ViaNase Electronic Atomizer from Kurve Technology (Bethell, Washington)). The intranasal delivery system from Kurve Technology is capable of accurately delivering a pre-determined drug volume (e.g., from 0.2-6 mL). The device is loaded and cleaned in the same manner as a pulmonary nebulizer. The device can deliver the drug to the olfactory region in bench testing, in animals and humans.

Male athymic nu/nu mice (6-8 weeks old) will be employed for this research. Rodent subcutaneous/intracranial glioma model can be established as follows. Six to eight week old athymic nu/nu mice will be anesthesized with intraperitoneal injections of ketamine (80 mg/kg) and xylazine (10 mg/kg). For the intracranial glioma model, the mice are placed into a stereotactic head frame (Harvard Apparatus), and local anesthetic (0.2 cc of 0.25% xylocaine) is injected into the right frontal scalp. A knife blade is used to make a small incision, and a drill bit is used to make a small opening in the right frontal skull at the level of the coronal suture. Glioma cells ($1\lambda10^5$ cells/10 µl), for example, U-87 human glioma cells, will be loaded into a calibrated Hamilton syringe. The needle tip will be placed precisely into the right frontal lobe of the rat, and cells will be slowly injected using a control push from the Hamilton syringe. After the injection is finished, the syringe and needle will be removed, and the wound closed.

Two weeks after surgical implantation, the mice will be divided into 4 groups (6 mice/group) and will be treated, respectively, with: saline drops alone (control), crude POH from Sigma (0.03%, 50 µl/drop, one drop per nostril), POH (purified to greater than 98.5% purity; 0.03%, 50 µl/drop, one drop per nostril), and TMZ (5 mg/kg, oral gavage). TMZ serves as the positive control.

Brains will be harvested, and tumor size determined. Survival curves will be constructed by following the mice until they develop neurological deficits. Our experience has been that survival is about four weeks after implantation for untreated mice, and up to 8 weeks for mice treated with TMZ.

We will also use an immune-competent syngeneic rat model where RG2 rat glioma cells ($1\times10^5$ cells/10 µl) will be implanted into the right frontal lobe of Fisher 344 rats. Rats will be divided into the same 4 groups as above. We will also examine the anti-invasion properties of POH using the rat RG2 model, because the RG2 cells can freely migrate, and thus, invade in the rat parenchyma.

Example 6

In a recent clinical research in Brazil, intranasal delivery of perillyl alcohol in patients with recurrent malignant gliomas resulted in regression or stabilization of the disease, with 50% of the 140 treated patients achieving 6 month progression-free period and several patients enjoying as many as 3 years of disease remission. Furthermore, side effects from the treatment were almost non-existent. Da Fonseca et al. Correlation of tumor topography and peritumoral edema of recurrent malignant gliomas with therapeutic response to intranasal administration of perillyl alcohol. *Invest New Drugs* 2009 Jan. 13.

We will deliver the purified POH (having greater than 98.5% purity) intranasally to patients suffering from malignant gliomas. To investigate whether POH can be delivered directly to the brain tumor cells, the distribution of the purified POH will be studied by delivering $^{11}$C labeled-POH to the patients, followed by positron emission tomography (PET) imaging. The patients will then undergo a limited therapeutic trial using escalating doses of inhalational POH. The patients will be dose escalated using groups of three, with each group receiving intranasal purified POH (with purity greater than 98.5%) at 0.05% (w/v), 1% (w/v), 1.5% (w/v), 2% (w/v), 2.5% (w/v). The 2% (w/v) is what is currently used in Brazil. Delivery will be via the ViaNase nasal inhaler and will be given three times per day. PET Imaging Studies. Ten patients with pathologically confirmed malignant glioma will be scanned following intranasal inhalation of 5-10 mCi of the $^{11}$C-POH formulation using a Siemens Biograph TruePoint HD PET/CT scanner. Static imaging will begin at 30 minutes following inhalation using 10-minute acquisition in a single bed position overlying the cranium. Subsequent serial acquisitions will occur at 30-minute intervals for 2 hours to assess progressive accumulation in brain and tumor tissue. Depending on patient compliance and levels of remaining and accumulated activity, we will attempt to image beyond 2 hours. Co-registered PET/CT images will be compared with contrast enhanced MRI studies on all patients to assess correlation of activity accumulation with enhancement patterns.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A method of treating a central nervous system (CNS) cancer, the method comprising administering to a mammal perillyl alcohol (POH) before or concurrently with a therapeutic agent that is a chimeric antigen receptor T-cell (CAR-T cell),
    wherein the POH and CAR-T cells are administered by intracardiac injection, and
    wherein the CNS cancer is a malignant glioma, pilocytic astrocytomas (grade I), meningiomas, metastatic brain tumors, or pituitary adenomas.

2. The method of claim 1, wherein the perillyl alcohol is administered at a dose ranging from about 0.050 mg/kg to about 500 mg/kg of a body weight of the mammal.

3. The method of claim 1, wherein the mammal is a human.

4. The method of claim 1, wherein the POH is administered from about 0.2 minutes to about 60 minutes before the CAR-T cell is administered.

5. The method of claim 1, wherein the POH is administered from about 1 minute to about 15 minutes before the CAR-T cell is administered.

6. The method of claim 1, wherein the POH and the CAR-T cell are administered separately.

7. The method of claim 1, wherein the POH and the CAR-T cell are administered concurrently.

8. The method of claim 7, wherein the POH and the CAR-T cell are administered together in a pharmaceutical composition.

9. The method of claim 1, wherein the CNS cancer is a malignant glioma.

10. The method of claim 9, wherein the malignant glioma is a glioblastoma, astrocytoma, or anaplastic astrocytoma.

11. The method of claim 9, wherein the malignant glioma is a glioblastoma.

12. The method of claim 1, further comprising treating the mammal with radiation.

13. The method of claim 1, wherein the CAR-T cell is a CD19 CAR-T cell or a Lym-1 CAR-T cell.

\* \* \* \* \*